(12) United States Patent
Zizi et al.

(10) Patent No.: US 12,229,235 B2
(45) Date of Patent: Feb. 18, 2025

(54) UNIQUE PATTERNS EXTRACTED FROM INVOLUNTARY EYE MOTIONS TO IDENTIFY INDIVIDUALS

(71) Applicant: Aerender Mobile, Inc., Mountain View, CA (US)

(72) Inventors: Martin Zizi, Palo Alto, CA (US); Brian Ebert, San Mateo, CA (US); Hugh Sharkey, Redwood City, CA (US)

(73) Assignee: Proprius Technolgies S.A.R.L, Luxembourg (LU)

( * ) Notice: Subject to any disclaimer, the term of this patent is extended or adjusted under 35 U.S.C. 154(b) by 364 days.

(21) Appl. No.: 17/890,158

(22) Filed: Aug. 17, 2022

(65) Prior Publication Data

US 2023/0083361 A1 Mar. 16, 2023

Related U.S. Application Data

(63) Continuation of application No. 15/806,094, filed on Nov. 7, 2017, now Pat. No. 11,544,359.
(Continued)

(51) Int. Cl.
*G06F 21/00* (2013.01)
*A61B 3/113* (2006.01)
(Continued)

(52) U.S. Cl.
CPC .............. *G06F 21/32* (2013.01); *A61B 3/113* (2013.01); *A61B 5/117* (2013.01); *G02C 7/04* (2013.01); *G02C 11/10* (2013.01); *G06F 3/013* (2013.01); *G06V 40/19* (2022.01); *G06V 40/197* (2022.01); *G06V 40/20* (2022.01)

(58) Field of Classification Search
None
See application file for complete search history.

(56) References Cited

U.S. PATENT DOCUMENTS 6,102,870 A * 8/2000 Edwards ............... A61B 5/163
600/558
7,630,524 B2 ‡ 12/2009 Lauper .................. G06V 40/18
382/117
(Continued)

FOREIGN PATENT DOCUMENTS

EP 0562742 A1 ‡ 9/1993
JP 2003-533801 ‡ 11/2003
(Continued)

OTHER PUBLICATIONS

Albrecht, Ronald; EPO Extended Search Report, EP17200539.9; Apr. 5, 2018; 10 pages.‡
(Continued)

*Primary Examiner* — Shin-Hon (Eric) Chen
(74) *Attorney, Agent, or Firm* — Alford Law Group, Inc.

(57) ABSTRACT

A method for user authentication is disclosed including capturing involuntary eye movement of an eyeball of a user; generating a unique pattern to identify the user in response to the involuntary eye movement; storing the unique pattern into a secured non-volatile memory device; and authenticating the user with an electronic device in response to the stored unique pattern.

9 Claims, 16 Drawing Sheets

Related U.S. Application Data

(60) Provisional application No. 62/419,458, filed on Nov. 8, 2016.

(51) Int. Cl.
*A61B 5/117* (2016.01)
*G02C 7/04* (2006.01)
*G02C 11/00* (2006.01)
*G06F 3/01* (2006.01)
*G06F 21/32* (2013.01)
*G06V 40/18* (2022.01)
*G06V 40/19* (2022.01)
*G06V 40/20* (2022.01)

(56) References Cited

U.S. PATENT DOCUMENTS

| | | | | |
|---|---|---|---|---|
| 8,184,867 | B2 ‡ | 5/2012 | Otto | G06K 9/00617 |
| | | | | 382/117 |
| 8,509,500 | B2 ‡ | 8/2013 | Yamada | G06V 40/1347 |
| | | | | 382/218 |
| 9,111,473 | B1 ‡ | 8/2015 | Ho | G06F 3/013 |
| 9,367,677 | B1 ‡ | 6/2016 | Adhami | G06F 21/32 |
| 9,953,149 | B2 ‡ | 4/2018 | Tussy | G06K 9/00288 |
| 2003/0091215 | A1 ‡ | 5/2003 | Lauper | G06V 40/18 |
| | | | | 382/117 |
| 2008/0104415 | A1 ‡ | 5/2008 | Palti-Wasserman | G06F 21/32 |
| | | | | 713/186 |
| 2010/0138668 | A1 * | 6/2010 | Tsuria | G06V 40/18 |
| | | | | 340/5.83 |
| 2013/0336547 | A1 ‡ | 12/2013 | Komogortsev | A61B 5/163 |
| | | | | 382/117 |
| 2014/0068270 | A1 * | 3/2014 | Shenoy | G06F 21/34 |
| | | | | 713/182 |
| 2014/0096077 | A1 * | 4/2014 | Jacob | G06F 3/013 |
| | | | | 715/810 |
| 2014/0125585 | A1 * | 5/2014 | Song | G06F 3/013 |
| | | | | 345/156 |
| 2014/0226131 | A1 * | 8/2014 | Lopez | G06F 21/31 |
| | | | | 351/210 |
| 2015/0227735 | A1 ‡ | 8/2015 | Chappell | G06F 21/32 |
| | | | | 726/19 |
| 2015/0294149 | A1 ‡ | 10/2015 | Palti-Wasserman | G06V 40/19 |
| | | | | 382/124 |
| 2015/0355815 | A1 ‡ | 12/2015 | Palti-Wasserman | G06F 3/013 |
| | | | | 715/835 |
| 2016/0235291 | A1 ‡ | 8/2016 | Goh | A61B 3/032 |
| 2016/0364881 | A1 * | 12/2016 | Mallinson | G06T 7/20 |
| 2017/0364732 | A1 ‡ | 12/2017 | Komogortsev | G06K 9/0061 |
| 2018/0089417 | A1 ‡ | 3/2018 | Liu | G02B 27/0093 |
| 2019/0065714 | A1 * | 2/2019 | Adams | G06F 21/32 |

FOREIGN PATENT DOCUMENTS

| | | | |
|---|---|---|---|
| JP | 2008-522652 | ‡ | 7/2008 |
| JP | 2010-061576 | ‡ | 3/2010 |
| WO | WO-WO2006061833 | ‡ | 6/2006 |

OTHER PUBLICATIONS

Moon, Nam-Du; Office Action Korean Intellectual Property Office; App. No. 10-2018-0051854; May 1, 2019 and English translation; 17 pages.‡

Selker et al.; "Eye-R, a Glasses-Mounted Eye Motion Detection Interface"; CHI 2001 CHI '01 Extended AbstrAts on Human Factors in Computing Systems; 2001, 2 pages.‡

Sensimed AG; "SENSIMED Triggerfish—24 hour profile of ocular dimensional changes"; 2013; 3 pages.‡

Liang et al., "Scaling of Horizontal and Vertical Fixational Eye Movements", Physical Review E 71, 031909, Mar. 21, 2005, p. 1-6.‡

Millodot, Michel; "Dicitionaly of Optometry and Visual Science", 7th Ed. ; 2009; p. 232, 4 pages.‡

Khushboo Shrivastava; "Presentation on Retina Scan"; Madhav Institute of Technology and Science; 2015-2015; 24 pages.‡

Onur Ferhat; "Eye-Tracking with Webcam-Based Setups: Implementation of a Real-Time System and an Analysis of Factors Affecting Performance"; Universitat Autonoma de Barcelona; 2012; 48 pages.‡

Pritchard, Roy M.; "Stabilized Images on the Retina"; Scientific American, Inc.; 1961; 7 pages.‡

Sensimed AG; Whitepapers—"SENSIMED Triggerfish provides reproducible 24 hour profile"; "Principles and rationale for the SENSIMED Triggerfish Sensor device"; "The "hyper" oxygen permeability characteristics (Dk/t) of the SENSIMED Triggerfish Sensor", "Rationale for single use of the SENSIMED Triggerfish Sensor"; 2013; 8 pages.‡

Keegan et al.; "An Electrooculogram-based Binary Saccade Sequence Classification (BSSC) Technique for Augmentative Communication and Control"; 31st Annual International Conference of the IEEE EMBS Minneapolis, Minnesota, USA, Sep. 2-6, 2009; 5 pages.‡

\* cited by examiner
‡ imported from a related application

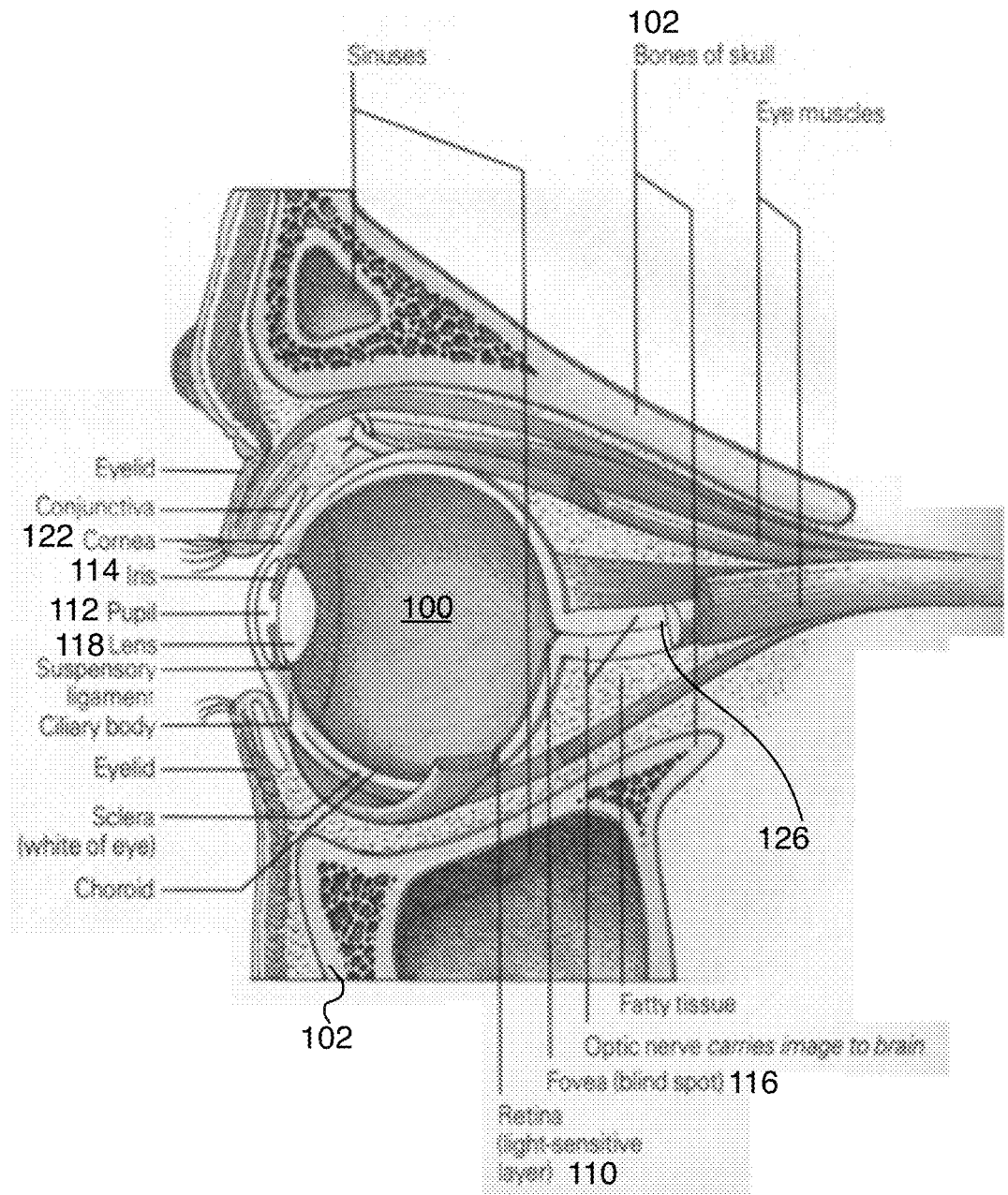

UNIQUE PATTERNS EXTRACTED FROM INVOLUNTARY EYE MOTIONS TO IDENTIFY INDIVIDUALS

CROSS REFERENCE

This United States (U.S.) patent application claims the benefit of U.S. Non-provisional patent application Ser. No. 15/806,094 titled UNIQUE PATTERNS EXTRACTED FROM INVOLUNTARY EYE MOTIONS TO IDENTIFY INDIVIDUALS filed on Nov. 7, 2017 by inventors Martin Zizi et al. U.S. patent application Ser. No. 15/806,094 claims the benefit of U.S. Provisional Patent Application No. 62/419,458 titled UNIQUE PATTERNS EXTRACTED FROM INVOLUNTARY EYE MOTIONS TO IDENTIFY INDIVIDUALS filed on Nov. 8, 2016 by inventors Martin Zizi et al.

FIELD

The embodiments of the invention relate generally to user identification and authentication.

BACKGROUND

Referring now to FIG. 1, a cross sectional view of a human eyeball 100 is shown within a skull 102. The human eyeball 100 is an imperfect globe that can be moved within the skull 102 by a plurality of muscles. The act or process of change in position of the human eyeball 100 within the skull 102 is referred to as eye movement or eye motion.

The eyeball 100 includes a retina 110, a pupil 112, an iris 114, a fovea 116, and a lens 118 that interact to capture color images for processing by the brain. A cornea 122 of the eyeball supports the pupil 112, iris 114, and lens 118 over the retina 110. The pupil 112 alters its diameter to adjust the amount of light received by the retina 110.

The retina 110 of the eyeball includes two types of photoreceptors, rods and cones. There are around 120 million cones and 6 to 7 million rods in the retina 110. Cones are concentrated in a rod free area of the retina referred to as the fovea centralis or macula that provides for maximum acuity and color sensitivity. The cones are smaller and more closely packed than elsewhere on the retina 110.

The optic nerve 126 is a cable of nerve fibers coupled to the eyeball that carries electrical signals from the rods and cones in the retina to the brain. The point where the optic nerve departs the eyeball through the retina is devoid of rods and cones. Thus, the optic nerve forms a "blind spot" in the retina.

FIGS. 2A-2C illustrate the plurality of muscles 202-202 coupled to the eyeball 100 to cause eye movement within the skull. In FIG. 2A, a left lateral rectus muscle 201L and a right lateral rectus muscle 201R pivot and move the eyeball 100 left and right horizontally as shown by the arrowhead 211. In FIG. 2B, a superior rectus muscle 201T on top and an inferior rectus muscle 201B on bottom pivot and move the eyeball 100 up and dawn vertically as shown by the arrowhead 212. In FIG. 2C, a superior oblique muscle 202S and an inferior oblique muscle 202I roll and move the eyeball 100 as shown by the curved arrowhead 213. These muscles can cause voluntary eye movement under the will of a human being and involuntary eye movement that the human being does not even know has occurred. Other muscles around the eyeball 100 may also contribute to voluntary and involuntary eye movement. The muscles are under control of the nervous system in a body including the brain.

Involuntary eye movement, in contrast to voluntary eye movement, is often considered to be a pathologic condition when observed clinically by an eye doctor. However, there are normal, physiologic, miniature-involuntary eye movements that occur and are more often observed during eye fixation on a target. These miniature-involuntary eye movements are a normal physiological function of the body to prevent fatigue of the rods and cones at the focal point on the retinal surface within the eyeball. Involuntary eye motions have typically been considered to be disturbances or analyzed for study purposes.

The retina 110 of the human eyeball 100 may scanned for various purposes. Retinal scanners that capture a two dimensional map of an anatomy of a retina of an eye are known. Retinal scanners were not intended to measure involuntary eye motion.

Various eye-tracking systems have been used to detect voluntary eye movement for a variety of purposes. For example, virtual reality headsets for gaming may track voluntary eye motion in game play of a video game. As another example, heads-up displays for military systems may track voluntary eye motion for some military purposes. However, eye tracking systems were intended to assess the foveal visual field and the focal attention of the subject and not measure involuntary eye motion, when the involuntary eye motions were considered to be either disturbances or for study purposes only.

BRIEF DESCRIPTIONS OF THE DRAWINGS

FIG. 1 is a cross section of an eyeball in the eye socket of a human skull.

DETAILED DESCRIPTION

In the following detailed description of the embodiments of the invention, numerous specific details are set forth in order to provide a thorough understanding. However, it will be obvious to one skilled in the art that the embodiments may be practiced without these specific details. In other instances well known methods, procedures, components, and circuits have not been described in detail so as not to unnecessarily obscure aspects of the embodiments.

Retinal sensitivity to photons is defined by genetic factors among others, by eye motions (eye movement), by eyeball muscles, and the integration of the whole system by specific brain wirings. Miniature involuntary eye movements of the eyeball 100 are a normal physiological function of the human body. Any neurologically mediated process will produce features that are unique ("proprietary") to the individual and therefore potentially useful in identifying one individual from another. Accordingly, the involuntary eye movements of the eyeball 100 are unique to an individual and can be used in user identification and user authentication. The embodiments described herein disclose methods and apparatus to uniquely identify a user in response to eye motions.

Figure 2A:
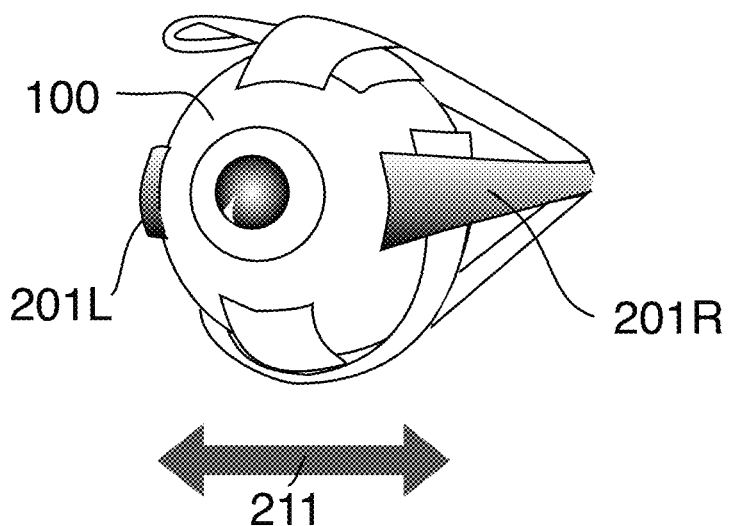
FIGS. 2A-2C are diagrams illustrating the various muscles coupled to the eyeball that cause various eye movements of the eyeball.
Figure 2B:
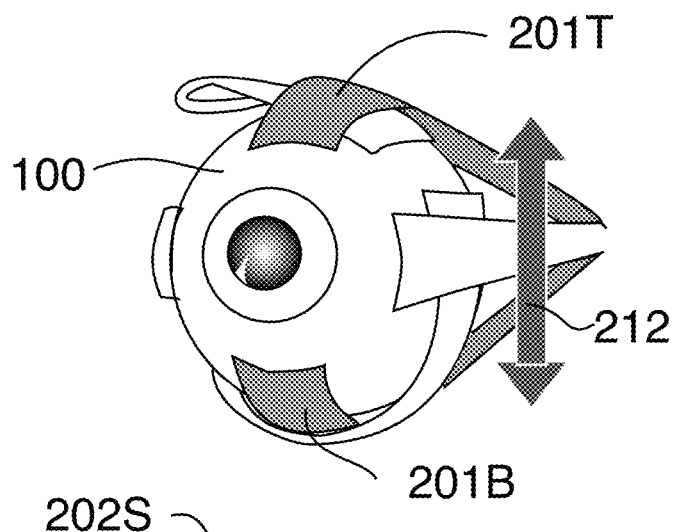
Figure 2C:
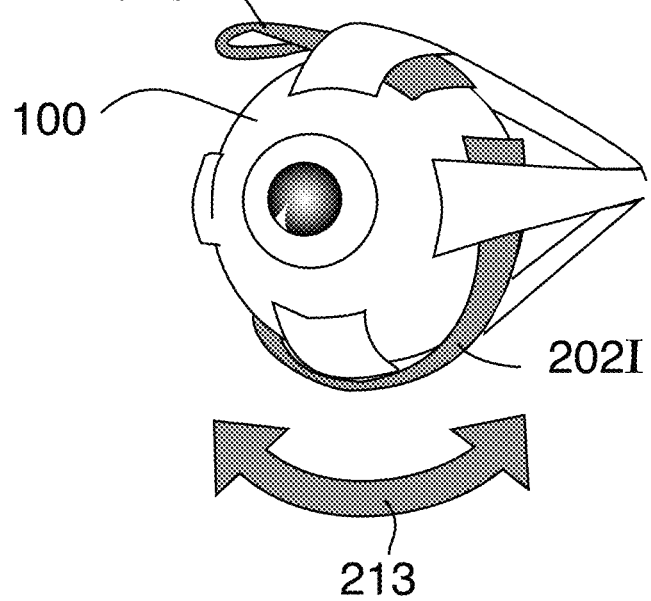
Figure 3:
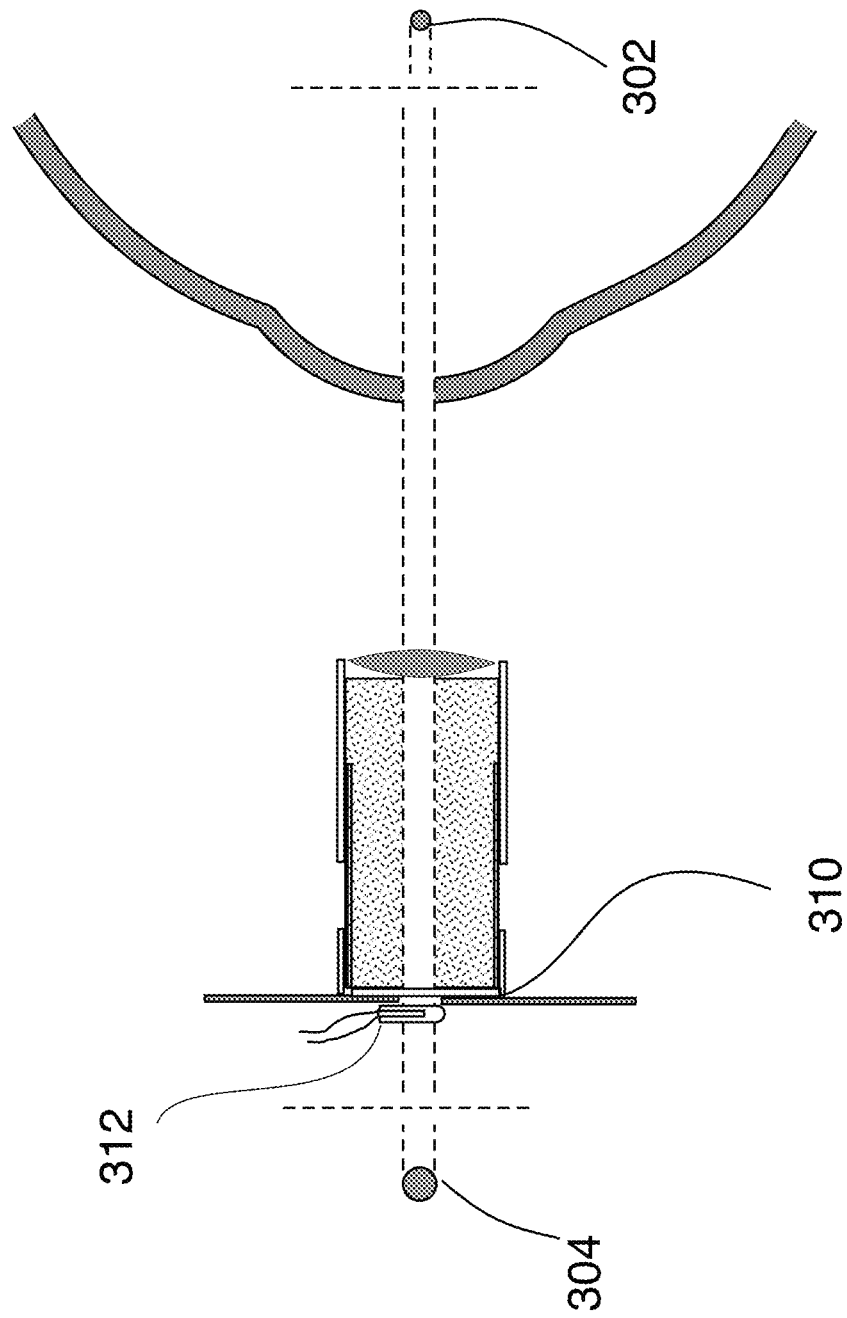
FIG. 3 is a diagram of the fixation process for capturing involuntary eye movements of the eyeball.

Referring now to FIG. 3, the small or miniature involuntary eye movements of the eyeball 100 can be captured by a fixation process of an eye on a target image 301. The target image 301 becomes a retinal image 302 on the retina 110 of the eyeball 100. The target image 301 can be generated by a target 304 on a display device 310. The user stares at or fixates on the target 304 on the display device 310 for a period of time (e.g., ten to fifteen seconds) during the fixation process. Involuntary movements are too small and subtle to be seen by direct observation with the naked eye. A video camera 312 captures a sequence of images of the movement of the eyeball 100 during the fixation process.

To avoid capturing voluntary eye movement during a fixation process, one may couple the camera 312 to the eyeball 100. However, this is impractical for authentication purposes. Voluntary eye movement can be substantially filtered out from the captured eye movement data to generate involuntary eye movement data.

Furthermore, while miniature involuntary eye movement (also referred to herein as involuntary eye micro-motions) has typically been captured during a fixation process, it can also be captured with large scale voluntary eye movement when the eyes are moving across a visual field, regardless of the focal point of interest. A video camera can be used to capture a sequence of images of large scale eye movement that includes the small scale or miniature involuntary eye movement. The miniature involuntary eye movement can be extracted from the captured sequence of images—that include both involuntary and voluntary eye movement.

Figure 4A:
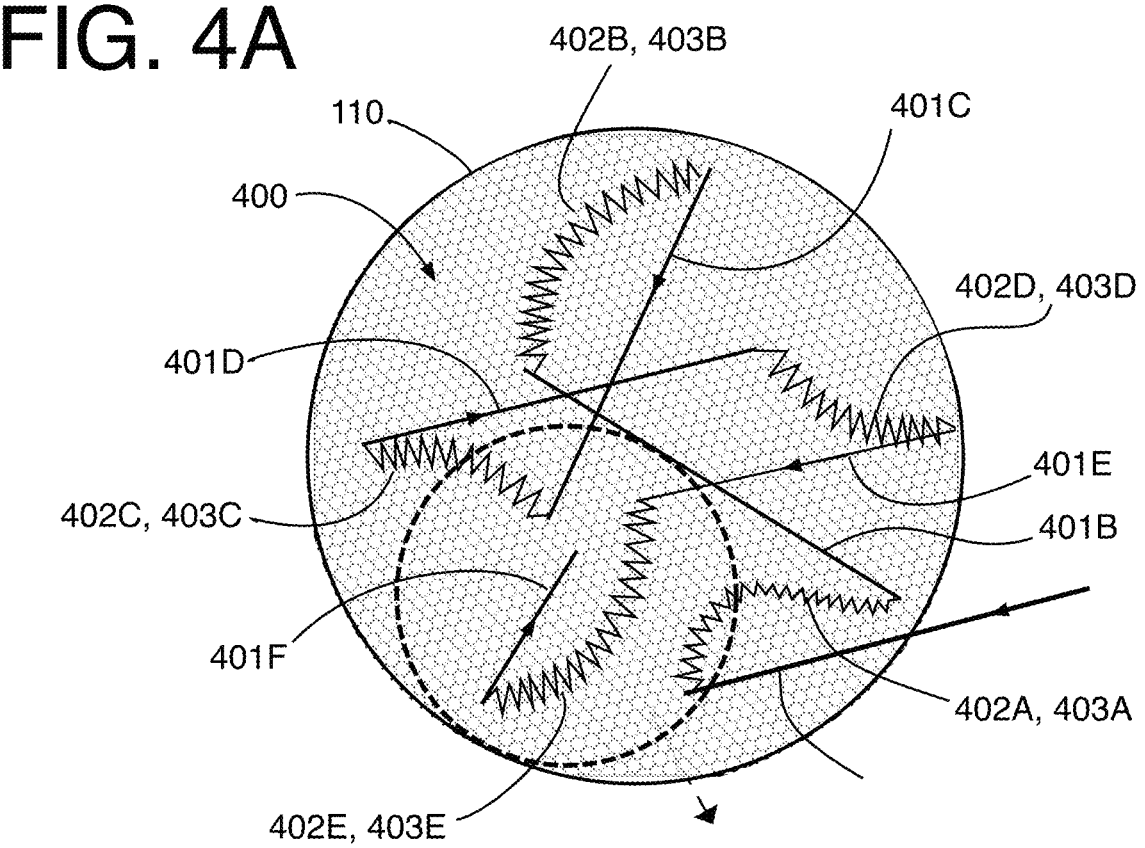
FIGS. 4A-4B are diagrams of magnified portions of the retina with a graph of involuntary eye movement charted over the zones of the cones in response to a user fixating on a target for a period of time.

In FIG. 4A, zones of cones 400 are shown a magnified portion of the fovea centralis in the retina 110. FIG. 4A further illustrates a graph of involuntary eye movement over the zones of the cones in response to a user fixating on a target for about ten seconds. FIG. 4A represents a plurality of cones within a diameter of about five microns of the retina 110.

Involuntary eye motions exist whether the subject or user fixates on a stationary object/target or not. The small involuntary eye motions include different types of eye movements, one of more of which can be used to identify a user.

Figure 4B:
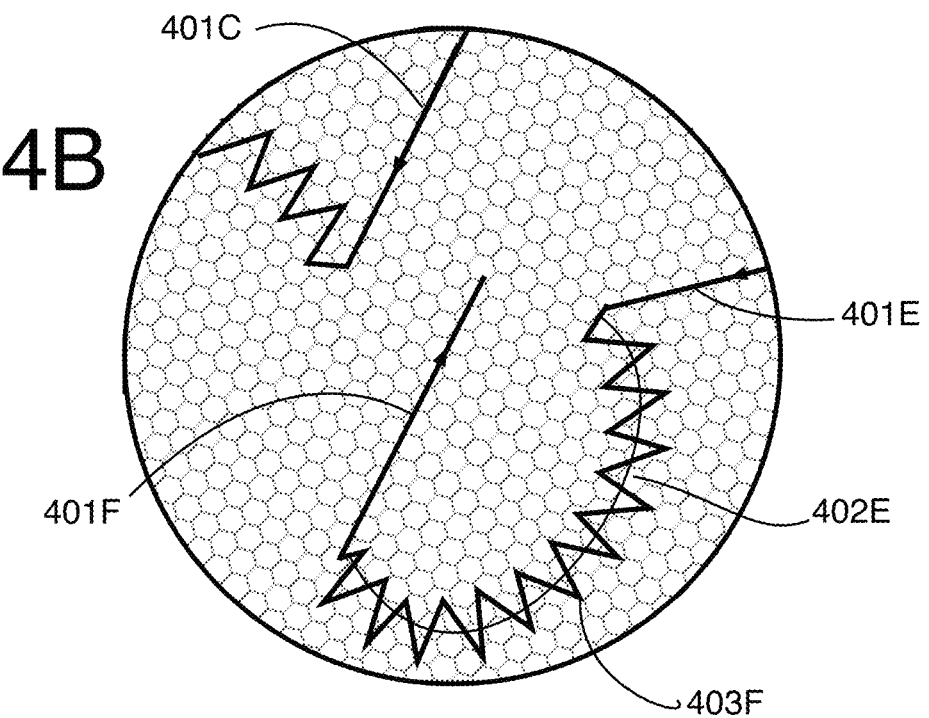

FIG. 4A illustrates the different types of small involuntary eye motions of interest, including saccades (also referred to as microsaccades) 401A-401F, curve shaped drifts 402A-402E, and zig-zag shaped tremors (also referred to as micronystagmus) 403A-403E. FIG. 4B illustrates a magnified view of the saccades 401F, curve shaped drift 402E, and the zig-zag shaped tremor 403E. The zig-zag shaped tremors 403E are imposed on the curved shaped drifts 402E.

The drift eye movements 402A-402E are like a random walk without any precise aim when the eyes are not focusing on anything in particular. They are characterized by a small amplitude motions with changing directions and by frequencies around 20-40 Hz. The tremor eye movements are characterized by a very small amplitude (e.g., 0.2 to 2-3 degrees of arc) and a higher frequency (e.g., 40-150 Hz, with 90 Hz being a typical value). The saccadic eye movements are characterized by an amplitude between 15-20 degrees of arc, a high speed (between 200-500 degrees per sec) and a relatively low frequency (e.g., from 0.1 Hz to between 1-5 Hz).

The miniature-involuntary eye movements are a normal physiological function of the body to prevent fatigue of the rods and cones at the focal point on the retinal surface within the eyeball. The image of a target or object on the retina of the eye is constantly moving due to the involuntary eye motions. The drift eye motion 402A-402E causes the image to drift slowly outward away from the center of the fovea. The drift eye motion terminates at the start of the saccadic eye movement. The saccadic eye movement 401A-401F brings the image back towards the center of the fovea. The tremor eye motion 403A-403E, superimposed on the drift eye motion 402A-402E, has an amplitude that crosses a plurality of cones to prevent exhaustion of a single cone when staring or fixating on the target.

These small involuntary eye movements are thought to prevent retinal fatigue. Retinal fatigue is the exhaustion of some key biochemical that is essential to the capture of photons by the retinal cells. The small involuntary eye movements are imperceptible to the naked eye. However, the involuntary eye movements can be captured and sensed/viewed/appreciated by retinal scanners and video cameras with sufficient speed to record eye movement, such as shown in FIG. 3 and FIG. 8B.

The involuntary eye motions/movements can be sensed by various means/methods such as by using an infrared light emitting diode (LED), pupil scanning methods, even refractometry, provided that these methods are modified to have the appropriate time/frequency and displacements resolution to capture the involuntary eye motions/movements.

The involuntary eye movements can alternatively be sensed using electrooculography with sufficient sensitivity to generate an electrooculogram (EOG) representative of the involuntary eye movement. The raw EOG signal originates in the dipole between the eye cornea and its retina.

Electrical signals also originate in the oculo-motor muscles when they cause the eye to generate eye movements. These electrical signals originating in the oculo-motor muscles themselves can be sensed to represent eye movement, similar to how to an electromyogram (EMG) from the eye.

Figure 7:
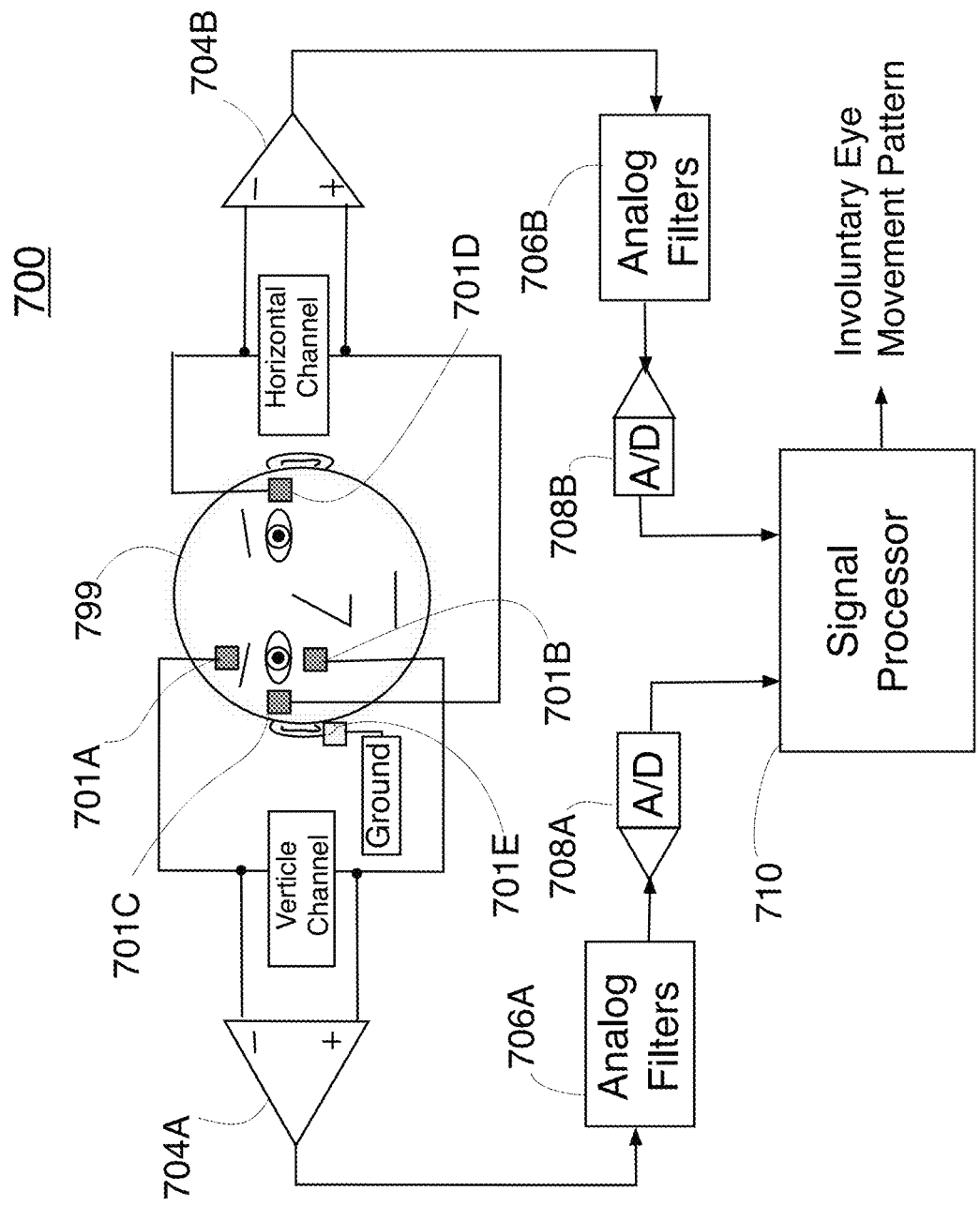
FIG. 7 is a block diagram of electrooculography system to directly generate signals of involuntary eye movements of a user.

Referring momentarily to FIG. 7, e electrooculography involves sensing electrical signals by measuring the potential difference (voltage) between the retina (grounded) and the cornea of the eye. Electrodes are typically placed around the eye to measure up, down, left, and right voltages with respect to one or more ground electrodes. Differences between left and right voltage measurements may be made to generate a signal indicating horizontal eye movement. Differences between up and down voltage measurements may be made to generate a signal indicating vertical eye movement. The signals can be amplified and filtered before signal processing occurs. The analog signals can be converted into digital signals so that digital signal processing can analyze the EOG signals for patterns in the involuntary eye movement of a user.

A pattern of the involuntary eye movement is employed as a method of performing a physiologic biometric identification of an individual because it is linked to the specific neuro-musculo-retinal anatomy of said individual. Capturing the micro-motions of the involuntary eye movements of the eyeball allows patterns to be extracted that are unique to the individual and can be used to authenticate the identity of an individual. These extracted patterns are analyzed and features extracted that provide a unique identifier of each individual. In accordance with one embodiment, a pupil is identified and tracked using a high speed, high resolution camera. The images are processed with a processor executing image processing software to extract the features from the involuntary eye movement that uniquely identify a user.

Involuntary eye movement can be used as a standalone method of authentication or in conjunction with retinal scanners that capture an image of the retinal anatomy of the eyeball. Involuntary eye movement can be also used as a method of authentication in conjunction with iris scanners that capture an image of iris anatomy of an eyeball. Involuntary eye movement can be also used as a method of authentication in conjunction with both retinal and/or iris scanners that capture images of eye anatomy.

Using both involuntary eye movement and retinal and/or iris anatomy provides for dual or triple authentication. Retinal and iris scanning technology does not include any neurologic component to the determination. Retinal scanning technology merely maps the anatomy of the retina to perform an authentication based on a two dimensional (2D) scan image. Involuntary eye movement adds a physiologic biometric parameter to the current eye scanning technology.

Prior art that analyzes eye movement can be distinguished from the embodiments disclosed herein.

United States (US) Patent Application Publication No. 2014/0331315, filed by Birk et al. on Dec. 23, 2011 (hereinafter Birk) discloses a method for deriving a biometric parameter from eye movements for use in authentication protocols; combining conventional authentication, such as "password or other information known to the user" as described in the Abstract, with eye movements based on a behavior repertoire consisting of actively moving the focus of the eye to "visually locate pieces of information embedded in a display" as described in the Abstract. The behavior repertoire in Birk may be either the path of the eye movements, or the characterization of the user's eye movements as they sequentially locate a sequence of numbers/letters to match a password or code known to the user.

Birk recognizes that there are several different types of eye movements both voluntary and involuntary. However, Birk describes using the only active, voluntary eye movements as an input for the recognition techniques disclosed therein. Birk essentially uses a defined grid, across which the user eyes must wander in a specific sequence to be recognized. Birk also makes use of a repertoire of motions (habits) specific to a given user.

In contrast to Birk, the embodiments disclosed herein utilize only the involuntary movements of the eye that occur as part of the normal eye physiology that are controlled by the brain stem and the cerebral cortex. The involuntary eye movements captured by the embodiments are not based on what the user does, but based on what the user is.

U.S. Pat. No. 6,785,406 issued to Mikio Kamada on Aug. 31, 2004 (hereinafter Kamada), describes an iris authentication apparatus for which they use some eye motions and iris contractions to ensure that the data are collected from a live user and not from just an image or some other body part. The eye motions used in Kamada are cycloversions, motions linked to the vestibular control of the eyes that ensure eye-head coordination when one looks at an object while the head is moving. Kamada also uses optokinetic nystagmus eye motion, which is a large saccade that brings back the fovea of the retina to center when an object drifts out of the visual field.

The eye motions described in Kamada are not micro-motions linked to the retinal fatigue and user-specific. The eye motions described in Kamada are reflexive motions. Kamada does not use eye motions to identify a user but to ascertain whether or not the data captured is from a live character. The eye motions described in Kamada are not user-specific so they cannot be used to identify a user because they are reflexive are like the knee jerk reflex, and present in every person, like a knee jerk reflex. Even though different strength levels may be recognized in Kamada, they are not fine enough to discriminate between individuals to provide identification.

U.S. Pat. No. 8,899,748 issued to Brandon Lousi Migdal on Dec. 2, 2014 (hereinafter Migdal), describes a method to detect reflex nystagmus eye motions linked to vestibular control (equilibrium) of an individual. However, vestibular nystagmus eye motions may be vertical or horizontal eye motions and originate as positional reflexes that are common. Moreover, vestibular nystagmus eye motions lack fine granularity of involuntary eye micro-motions that are useful in discriminating between individuals by the embodiments disclosed herein.

U.S. Pat. No. 9,195,890, issued to James R. Bergen on Nov. 24, 2015 (hereinafter Bergen), discloses a biometric identification method based on iris image comparisons. Bergen's comparison is based on extracted and unique anatomical features of the irises of eyes. The features of the irises are resolved at various depths of detail by Bergen. In order to align and match an iris to a stored iris pattern, Bergen must correct for motions and for tilts/positions, as well as correct for other image distortions. The eye motions referred to in Bergen are large scale and are undesirable because they represent a hindrance to acquiring quality data in Bergen's iris recognition system. This is contrary to the embodiments disclosed herein.

U.S. Pat. No. 7,336,806 issued to Schonberg et al. (hereinafter Schonberg); discloses iris-based recognition of a user for which the annulus circumference is key. Schonberg considers other features, including eye motion, to be noise that is to be eliminated.

U.S. Pat. No. 7,665,845 issued to Kiderman et al. on Feb. 23, 2010 (hereinafter Kiderman) describes a video-oculographic (VOG) system that is (VOG) based on light weight goggles. Kiderman's goggles were designed to make clinical measurements unbiased by the weight of the measuring instrument. However, Kiderman does not disclose using involuntary eye micro-motions that are of interest in the embodiments disclosed herein. Moreover, there is no obvious need for spatial resolution with regards to the embodiments disclosed herein.

Eye Movement Detection

Electrooculography can directly generate signals of involuntary eye movements. When using captured video images to track eye movements, a viewable feature of the eyeball in the video images is used. Pattern recognition may be used to detect the viewable feature in each image of the video images.

Figure 6A:
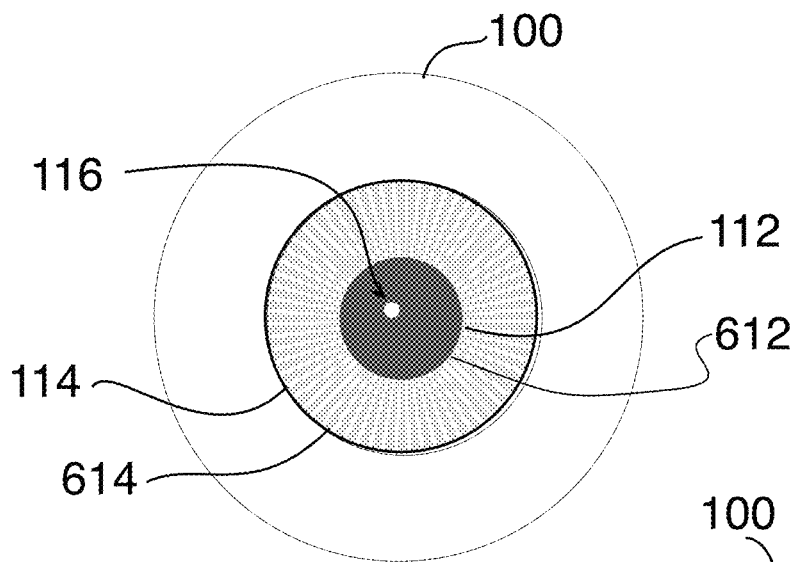
FIGS. 6A-6C are diagrams of the viewable features in video images of the eyeball that may be used to detect involuntary eye movements.

Referring now to FIGS. 6A, the viewable feature in the images of the eyeball may be the iris 114, the pupil 112, or the fovea 116. Edge detection may be used to track involuntary eye movements from video images of the eyeball 100 captured while a user fixates on a target. Edge detection can be taken from the circumference 614 of the iris 114, the circumference 612 of the pupil 112, or the location of the fovea 116.

Figure 6B:
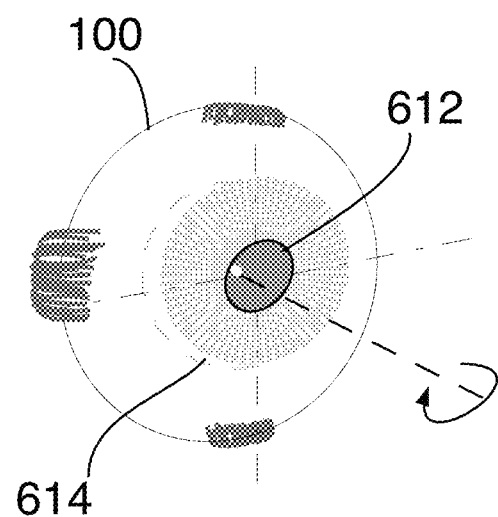

As shown in FIG. 6B, the circumference 614 of the iris 114 is useful to track involuntary eye movements because it is well defined and consistent. The circumference 612 of the pupil 112 may alternatively be used to track involuntary eye movements. However, the size and location of the pupil changes in response to light intensity.

Figure 6C:
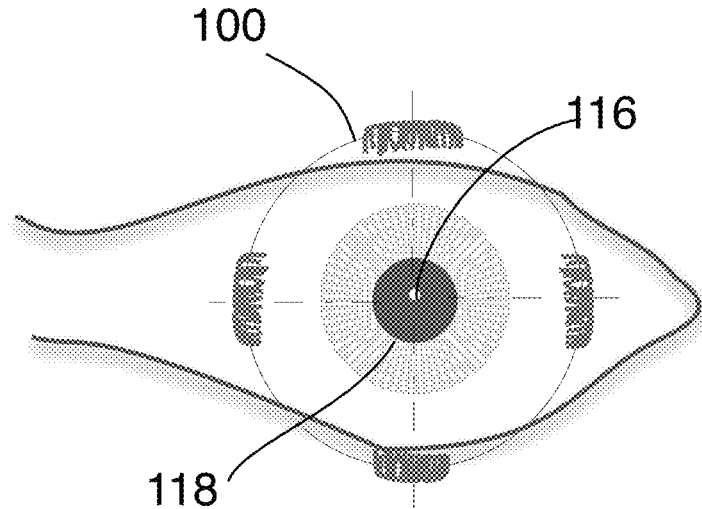

As shown in FIG. 6C, the fovea 116 may alternatively be used to track involuntary eye movements. However, tracking the fovea 116 typically requires a light source shined through the lens 118 to illuminate the retina 110 of the eyeball 100.

Figure 5A:
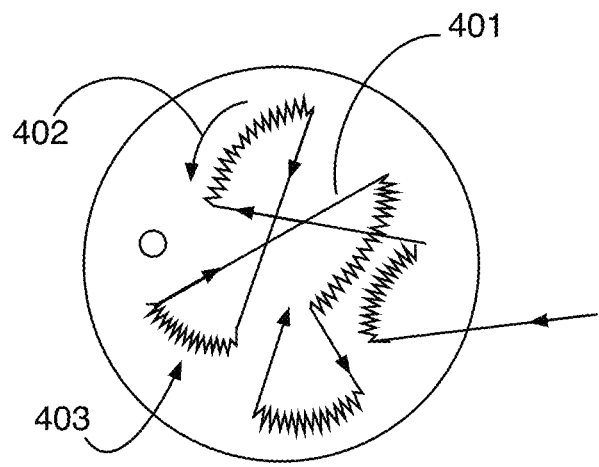
FIGS. 5A-5C are diagrams illustrating various combinations of the involuntary eye movements that can be used for user identification and authentication.
Figure 5B:
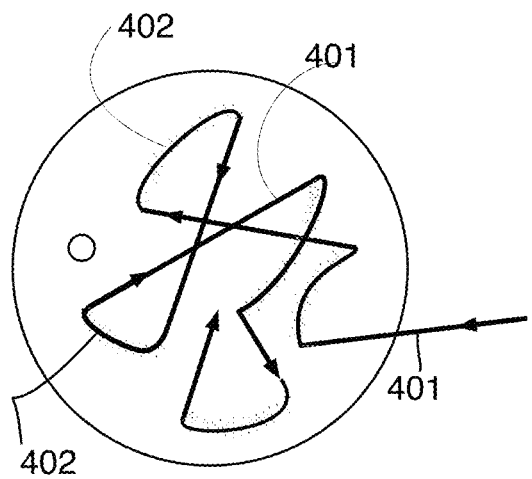
Figure 5C:
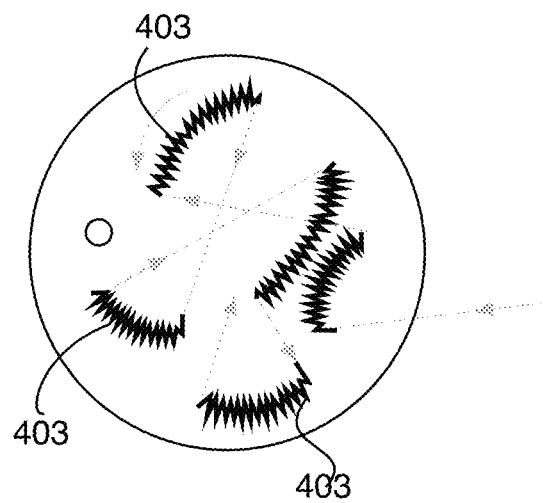

Referring now to FIGS. 5A-5C, various combinations of the involuntary eye movements can be used for user identification and authentication.

In FIG. 5A, all three types of involuntary eye movement, including saccade trajectories, drift, and tremors, are used to determine a unique identifier of each user. In accordance with one embodiment, features are extracted from all three involuntary eye movements to uniquely identify each user. The system is consistent in extracting the same features over and over again for each user.

In FIG. 5B, two involuntary eye movements, such as saccade trajectories and drift, are used to determine a unique identifier of each user. In accordance with another embodiment, features are extracted from saccade trajectories and drift to determine a uniquely identify each user. The system is consistent in extracting the same features over and over again for each user.

In FIG. 5C, a single involuntary eye movement, such as the tremor component, is used to determine a unique identifier of each user. In accordance with yet another embodiment, features are extracted from the tremor component of the involuntary eye movements to uniquely identify each user. The system is consistent in extracting the same features over and over again for each user.

Referring now to FIG. 7 an exemplary electrooculography system 700 is shown to directly generate signals of the involuntary eye movements of a user 799. A plurality of electrodes 701A-701E are applied near the eyes around a users head/face to capture voltages around each eye during eye movement. The electrodes may be part of a hood or a face receiving device to couple the electrodes to the surface of the user's head/face. Electrodes 701A-701B capture the up and down or vertical motion of the eyeball 100. Electrodes 701C-701D capture the left and right or horizontal motion of the eyeball 100. One or more electrodes 701E provide a ground or zero voltage reference for each electrode 701-701D. The electrodes 701A-701D measure up, down, left, and right voltages with respect to the one or more ground electrodes 701E as involuntary eye movement occurs during the fixation process.

The up and down voltages of electrodes 701A-701B with or without filtering are coupled into the negative and positive inputs of a difference amplifier 704A to amplify and compute the difference between the up and down voltages. This forms a vertical eye movement signal. The vertical eye movement signal may be coupled into analog filters 706A to remove noise and other unwanted signals to additionally emphasize the vertical eye movement signal. The filtered vertical eye movement signal, an analog signal, is coupled into a analog to digital converter 708A to convert the analog form into a digital form of signal. The digital filtered vertical eye movement signal is coupled into a first parallel digital input of a digital signal processor 710. In an alternate embodiment, the signal processor can be manufactured to support mixed analog and digital signals. Accordingly, the signal processor 710 can include be used Similarly, left and right voltages of electrodes 701C-701D with or without filtering are coupled into the negative and positive inputs of a difference amplifier 704B to amplify and compute the difference between the left and right voltages. This forms a horizontal eye movement signal. The horizontal eye movement signal may be coupled into analog filters 706B to remove noise and other unwanted signals to additionally emphasize the horizontal eye movement signal. The filtered horizontal eye movement signal, an analog signal, is coupled into a analog to digital converter 708B to convert the analog form into a digital form of signal. The digital filtered horizontal eye movement signal is coupled into a second parallel digital input of the digital signal processor 710.

The digital signal processor 710 performs digital signal processing using both the digital filtered horizontal eye movement signal and the digital filtered vertical eye movement signal to analyze, extract features, and generate the unique identifying pattern from the involuntary eye movement of the user. In this case, the unique identifying pattern of involuntary eye movement is directly captured from the user's head/face without using a video camera or scanner and analyzing images.

Figure 8A:
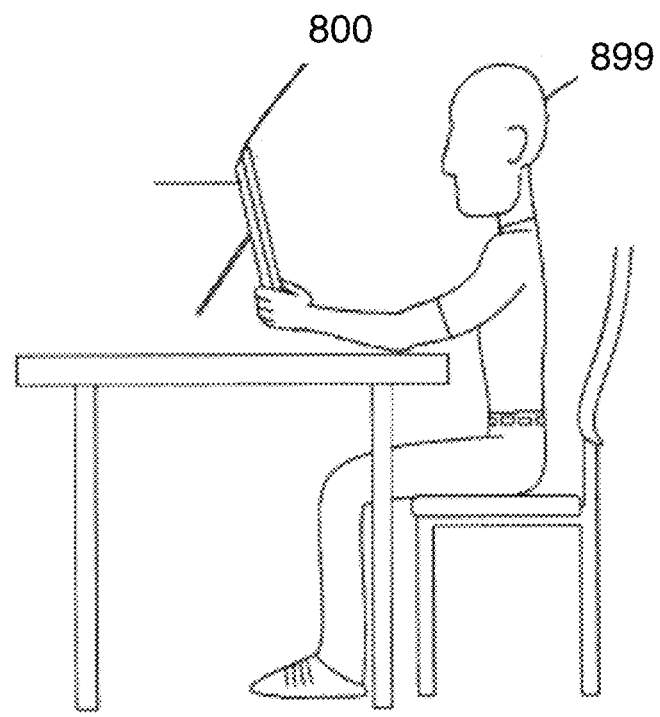
FIG. 8A is a diagram of an electronic device with a video camera that may be used to capture images of eye movement of a user.
Figure 8B:
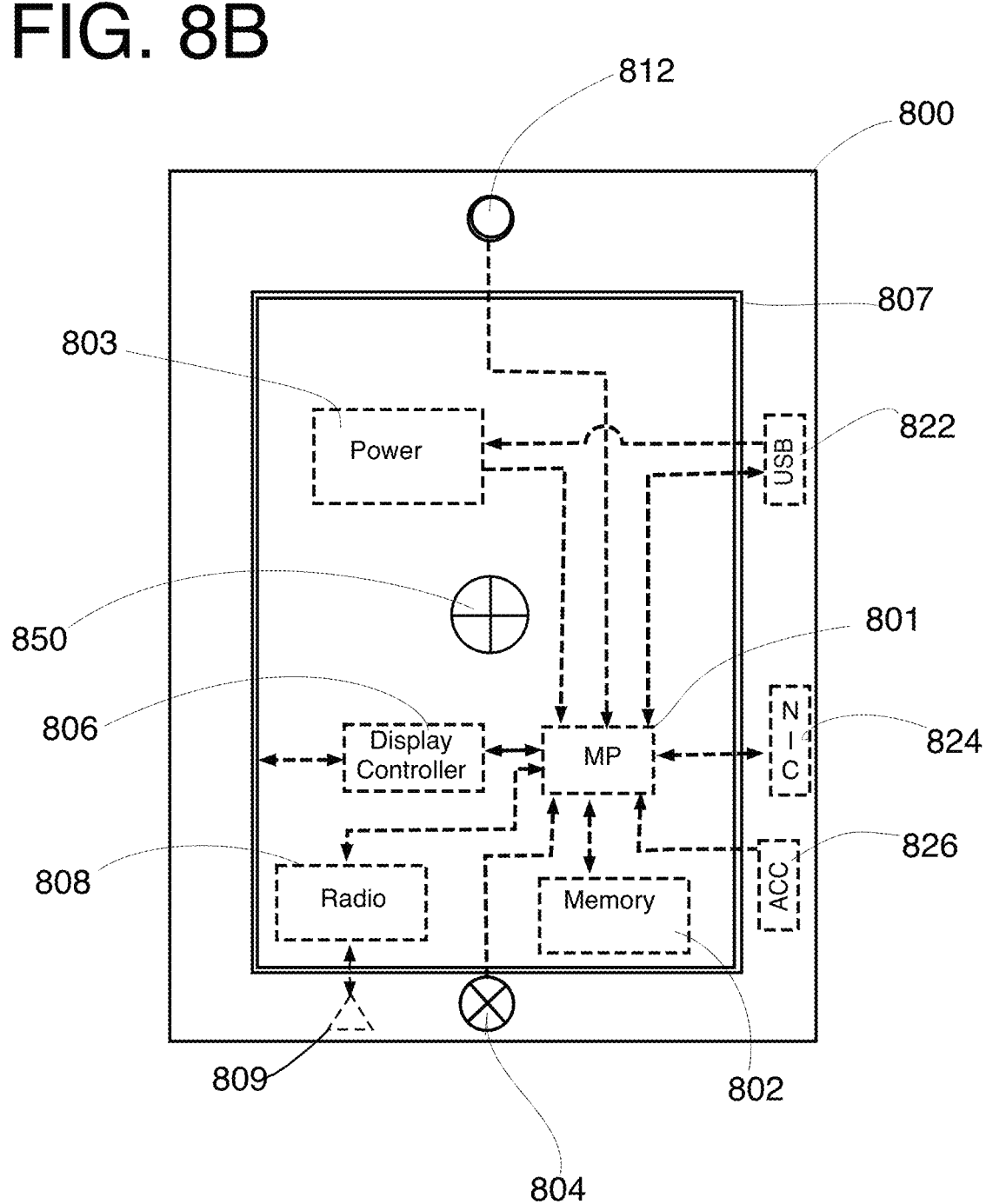
FIG. 8B is a block diagram of the electronic device with the video camera shown in FIG. 8A that may be used to capture images of eye movement of the user.

Referring now to FIG. 8A-8B, an electronic device 800 with a video camera is used to capture images of eye movement of the user 899 during the fixation process.

In FIG. 8B, the electronic device 800 includes a display device 807 and a video camera 812 coupled to a processor, microcomputer, or microprocessor (up) 801. The electronic device 800 further includes a memory 802 to store program instructions and user associated data. The electronic device 800 may further one or more (radio frequency transmitters/receivers) radios 809 and one or more wired connectors 822,824 (e.g., USB port 822, and/or network interface port 824) to provide communication between the electronic device 800 and other electronic devices by wireless or wired means. The electronic device 800 further includes a touch screen display device 807 to provide a displayable user interface UI to the user using the electronic device 800.

Software controls can be displayed on the touch screen display device 807 so the user can control the electronic device. The electronic device 800 can optionally include one or more hardware buttons 804 to further allow the user to control the electronic device.

In support of capturing eye movement, the processor 801 generates a fixation target 850 that is displayed by the display device 807. A user is asked to fixate on the fixation target 850 while the video camera 812, under control of the processor 801, captures a temporal sequence of images, a video, of the users eyes. The video, from frame to frame, captures the involuntary eye movement of one or both eyeballs of the user. 3D accelerometer data is captured with the video to remove physical movements of the camera 812 and the electronic device 800 from determining eye movement.

The processor 801 includes or may be adapted to provide signal processor functionality. In any case, the processor executes instructions of pattern recognition software and signal processing software to analyze the video capturing the involuntary eye movement of one or both eyeballs of the user. The pattern recognition software may be used to identify the eyeballs in the video and then the irises and pupils in the video.

The captured video is analyzed to detect if a user blinks during the temporal sequence of images and whether or not a sufficient sequence is captured detect involuntary eye movements. If not, the user is asked by the user interface to repeat the fixation process.

If a sufficient sequence of images is captured, further analysis is performed to determine the movement of the eyeball from image to image. A reference point on the eyeball, such as the iris or pupil, is used to determine the involuntary movement in the captured video of the fixation or staring process. The 3D accelerometer data is used to exclude the physical movement of camera 812 captured in the video from the raw eyeball movement data to form true eyeball movement data.

The true eyeball movement data is further analyzed to extract the desired type of involuntary eye movement data that is to be used in authenticating and/or uniquely identifying the user.

A user is initialized to the electronic device 800 to store an initial data set of initial captured involuntary eye movement data. From the initial data set, features linked to the time-series of the involuntary eye motions are extracted and classified to be associated with the user.

Subsequently features extracted from captured data sets of newly captured involuntary eye movement data are compared against the associated stored features extracted from the initial captured involuntary movement data to identify a user. A match percentage can be calculated to determine if the user is authorized to use the electronic device.

The newly captured involuntary eye movement data is compared against the initial captured involuntary movement data to determine match results. If the match results are within a match percentage, the user is identified and authorized to use the device. If the match results are outside the match percentage, the user is unidentified and not authorized to use the device.

Involuntary eye motions (e.g., tremors) can occur at about a maximum frequency of 150 Hertz (Hz) or cycles per second. Cones of an eye range in diameter from 0.5 to 4 micro-meters (microns). To capture the desired involuntary eye motions, appropriate recording devices in systems, such as the video camera 812 coupled to the processor 801 in the electronic device 800, operate at a minimum frame rate (frames per second) of at least a range of 300 Hz-450 Hz and optimally at a frame rate of 1000 Hz or more. Cameras and processors in pre-existing electronic devices may be re-programmed by a software application or driver to run faster than the typical setting. Normal (large scale saccade) covers 300 degrees per second and can re-align the eyes within a third of a second. Whereas involuntary micro-saccades cover a few degrees per second down to 0.2 degrees in amplitude. Accordingly, the spatial resolution of recording devices that can resolve down to within the range of 0.1-0.2 degrees can be optimal for capturing the desired involuntary eye motions.

While one type of electronic device 800 is shown in FIGS. 8A-8B for capturing the desired involuntary eye motions, other types of electronic devices can be used to capture the desired involuntary eye motions. FIGS. 9A-11C illustrate other means and electronic devices to capture the desired involuntary eye motions.

Figure 9A:
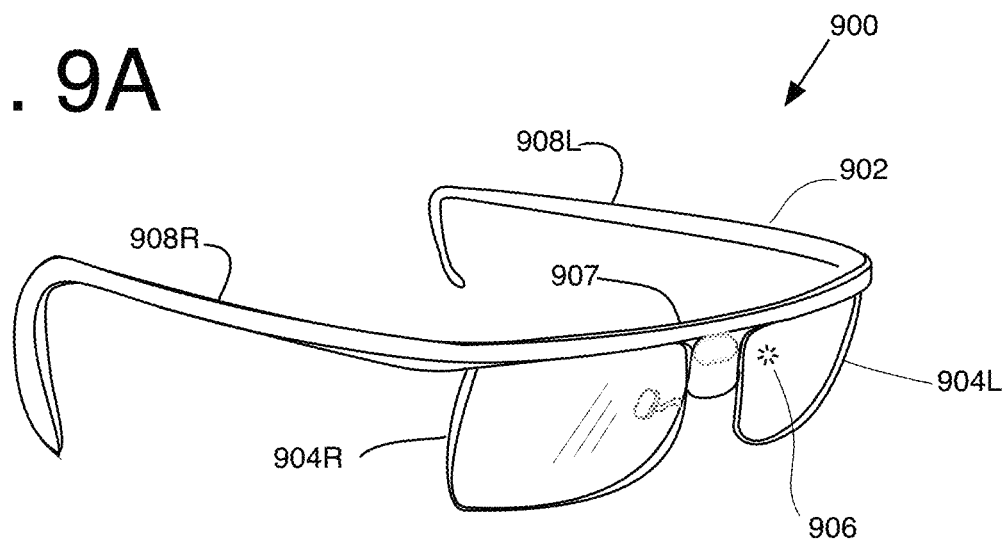
FIGS. 9A-9B are diagrams of electronic glasses with a video camera that may be used to capture images of eye movement of a user.
Figure 9B:
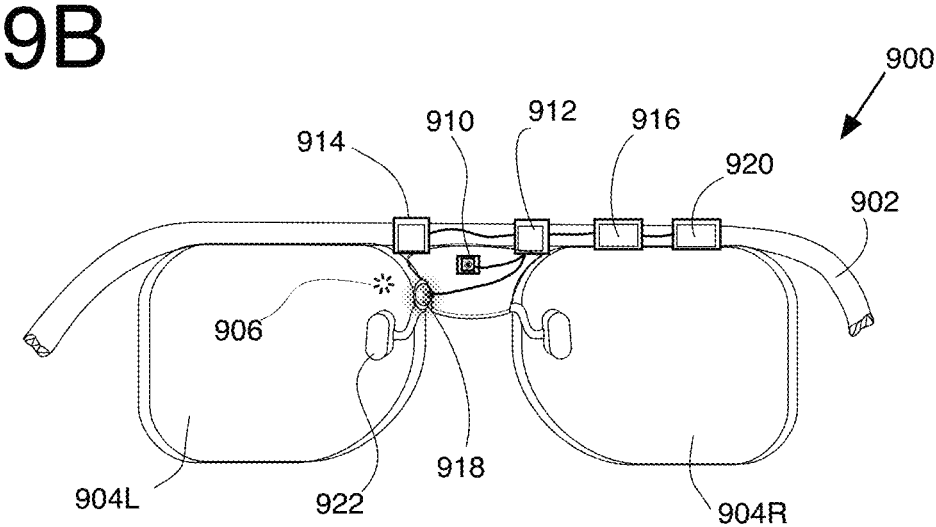

Referring now to FIGS. 9A-9B, electronic glasses 900 are shown that may be used to capture images of eye movement of a user. From the captured images of eye movement, the small scale involuntary eye motions can be extracted. The electronic glasses 900 may be temporarily worn by a user in order to identify, authenticate, and authorize a user to a system or apparatus.

The electronic glasses 900 include an eye glass frame 902 to which a left lens 904L and a right lens 904R are mounted in a pair of eye wires. In accordance with one embodiment, the eye glass frame 902 includes a bridge 907, a left temple 908L, a right temple 908R, nose pads, nose pad arms, and the pair of eye wires. They electronic glasses 900 may alternatively be clip on glasses worn over prescription glasses. The lenses 904L-904R may be prescription lenses or not.

A small target 906 may be formed in an upper right corner of the left lens 904L to direct a user's eyes towards a video camera. Alternatively, the target 906 could be formed in an upper left corner of the right lens 904R to direct the user's eyes towards the video camera. The target 906 can be formed on either lens by printing a target image onto the surface of the lens, by inscribing the target image into the lens, by shining a target light onto the surface of the lens; or by other known means of applying an image onto a clear surface.

Figure 9C:
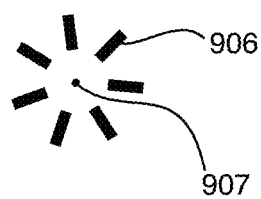
FIG. 9C is a magnified view of a target that may be used with the electronic glasses of FIGS. 9A-9B.

Referring momentarily to FIG. 9C, the target 906 is a short depth-of-field target with a center opening or hole 907. With the target 906 on the lens 904L or 904R, it is too close for the user to focus on. However, the user can focus through the center opening 907 of the target 906. The target 906 with its center opening 907 acts like an optical tether so that the pupil is located in line with the video camera to better capture eye movement.

Referring now to FIG. 9B, the electronic glasses 900 further includes the video camera 910, a processor 912, a memory device 914, a radio transmitter/receiver (transceiver) 916, and a power supply (e.g., battery) 920 mounted to the eye glass frame 902. The electronic glasses 900 may further include an optional light emitting diode (LED) 918 mounted to the frame 902 or a nose pad arm 922.

The video camera 910 is angled slightly towards the lens with the target, such as the left lens 904L with the target 906, so that it is more in line with the eye when focusing on the target. The video camera 910 and processor 912 operate together at a frame rate in the range of a 300 to 1000 frames per second to capture involuntary eye motions at a maximum frequency of 150 Hz.

The radio 916 may be used by the processor to communicate with a computer or server to authenticate the user to the computer or server. The memory 914 may be used to store initialization data, including the initial involuntary eye motion features that are extracted from the captured eye motions.

The electronic eyeglasses 900 may be temporarily worn by the user to authenticate the user to a system. In the alternative, electronic goggles may be used.

Figure 10A:
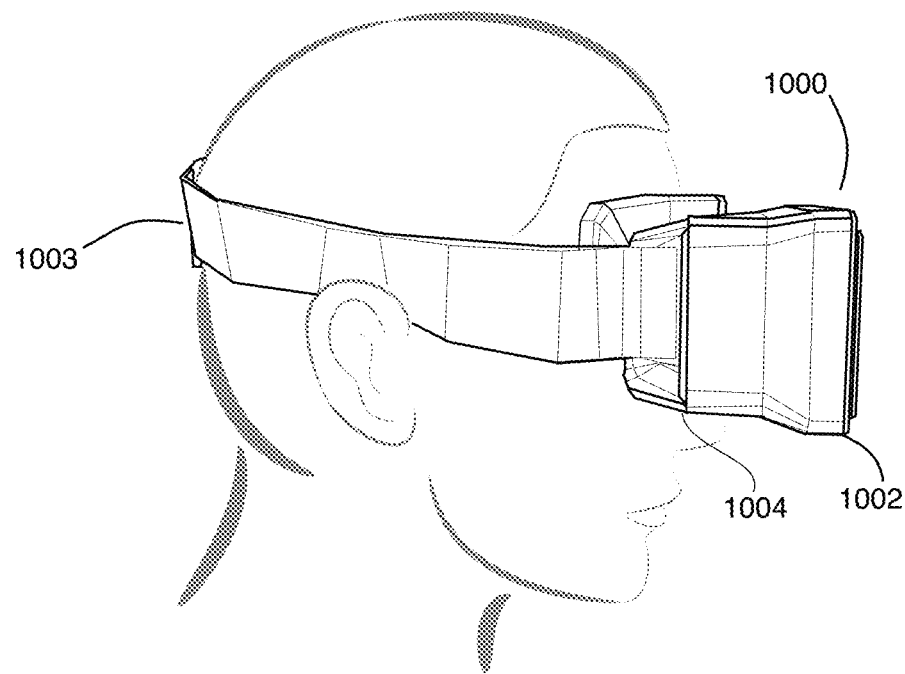
FIGS. 10A-10B are diagrams of virtual reality goggles with a video camera that may be used to capture images of eye movement of a user.
Figure 10B:
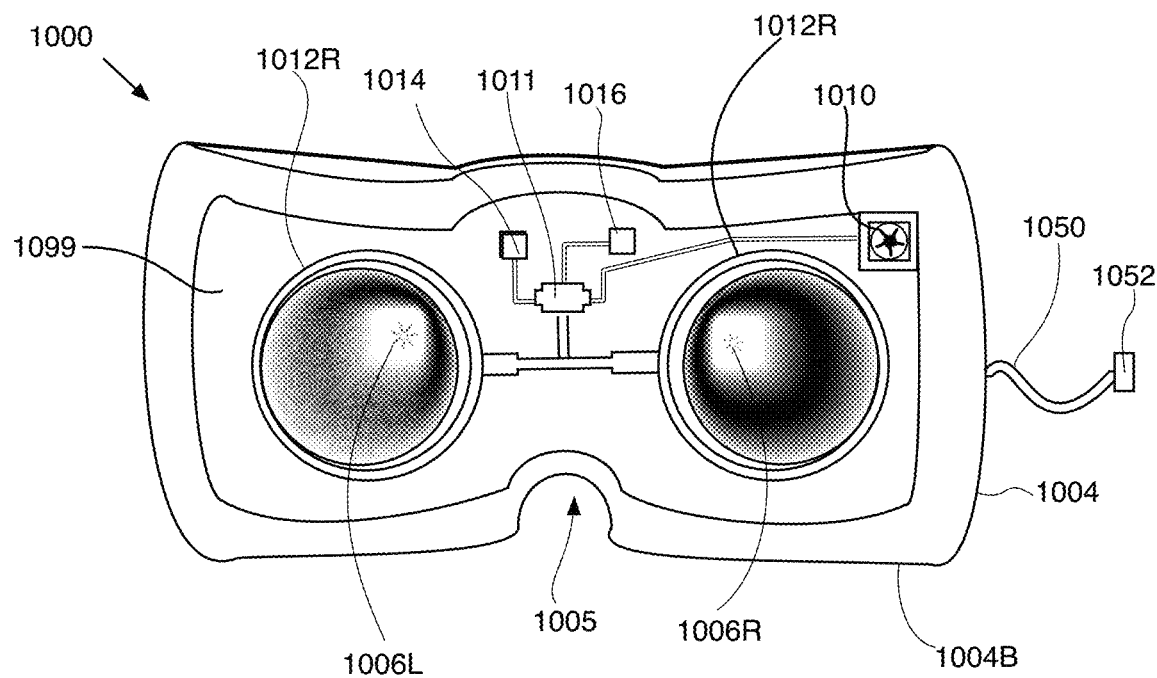

Referring now to FIGS. 10A-10B, electronic virtual reality headset or goggles 1000 including a video camera that may be used to capture eye motion of an eye of a user. The electronic virtual reality headset includes a frame 1002 and a head strap 1003 to retain the headset affixed to the users head. The frame 1002 includes top, bottom, left, and right flexible curtains or blinders 1004 configured to receive the face around the eyes of the user to provide a hooded area 1099 to keep outside light from entering. The bottom curtain or blinder 1004B includes a nose opening 1005 to receive the nose of a user.

In FIG. 10B, the headset 1000 further includes the video camera 1010, a left display device 1012L, and a right display device 1012R coupled to the frame 1002. The headset 1000 further includes a processor 1011 and a memory 1014 coupled together. The video camera 1010 and the left and right display devices 1012L,1012R are coupled to the processor 1011. The left display device 1012L and the right display device 1012R can provide a stereo three dimensional image to the user at varying perceived depths. The video camera 1010 may be coupled to the frame 1002 inside the hooded area 1099 at different locations to capture eye motion. The video camera 1010 may be located on the right as shown to capture eye motion to avoid interfering with the video images displayed by the left and right display devices 1012L,1012R. In an alternate embodiment, a pair of video cameras 1010 may be located on opposite sides to capture eye motions of both left and right eyes so that the involuntary eye micro-motions from one or both eyes are used to authenticate a user.

A stereo three dimensional target comprising a left target 1006L and a right target 1006R may be generated by the processor 1011 and displayed on the left display device 1012L and the right display device 1012R, respectively. The left target 1006L and the right target 1006R can cause the target to appear far away to focus the eyes at a distant and somewhat fixate the eyes to better capture involuntary eye movement with the video camera 1010.

The processor 1011 may be wired by a cable 1050 and plug 1052 to another system. Alternatively, a radio transmitter/receiver (transceiver) 1016 may be coupled to the processor 1011 so that the processor and headset/goggles can wirelessly be coupled to another system to use the authentication capability of the headset/goggles 1000.

Figure 11A:
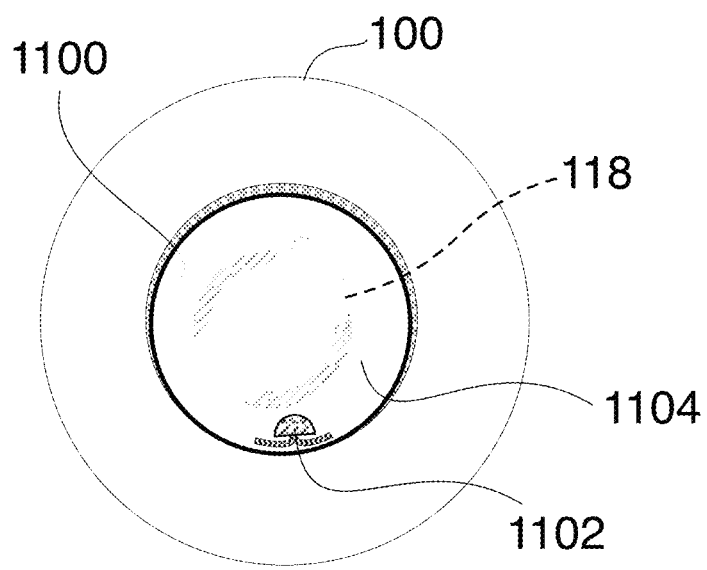
FIG. 11A is a diagram of an eyeball with a contact lens with an emitter device that may be used to aid in the capture of data regarding eye movement of a user.

Referring now to FIG. 11A, eye motion can be captured in another manner by using a contact lens 1100 mounted to one or both eyes 100 of a user over the lens 118. The contract lens 1100 includes one or more emitters 1102 coupled to (e.g., embedded in or printed on) the lens material 1104. The emitter 1102 may be an active device, such as a light emitting diode or a radio beacon with associated driving circuits (e.g., radio transmitter/receiver, diode driver); or a passive device, such as a reflector, retro-reflector, or mirror.

In the case of an active emitter device, one or more sensors are used to receive the emitted light or radio signal to determine position of the eye from one time point to the next to directly capture eye motion over a period of time. Power may be wirelessly coupled from a base antenna around the eye into an antenna coupled to the active emitter device in the contact lens. Radio signals may also be coupled between the base antenna and the antenna coupled to the active integrated circuit device. A three dimensional motion sensor may be included as part of the integrated circuit to capture eye motion including the involuntary eye micro-motions of interest.

In the case of the passive emitter device, light of a light source is directed to the passive emitter device to activate it into reflecting light back to one or more photo diode sensors around the eye. A combination of active emitter devices and passive emitter devices may be used in the same contact lens to capture eye motion by either or both means.

Figure 11B:
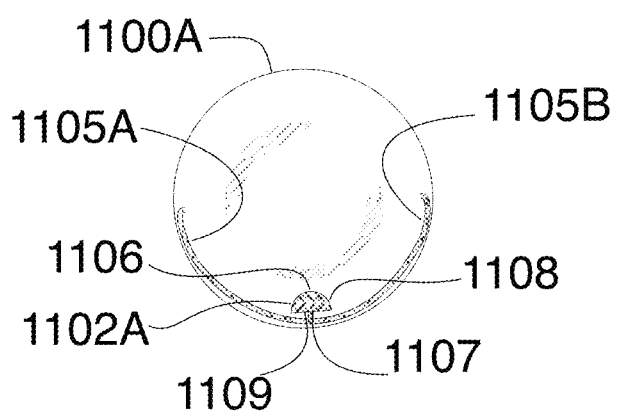
FIGS. 11B-11D are diagrams that illustrate contact lenses with various emitter devices that may be used to aid in the capture of data regarding eye movement of a user.
Figure 11C:
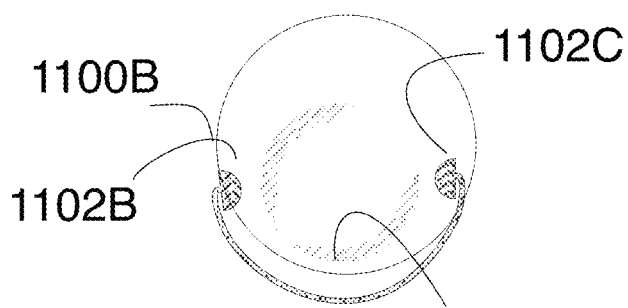
Figure 11D:
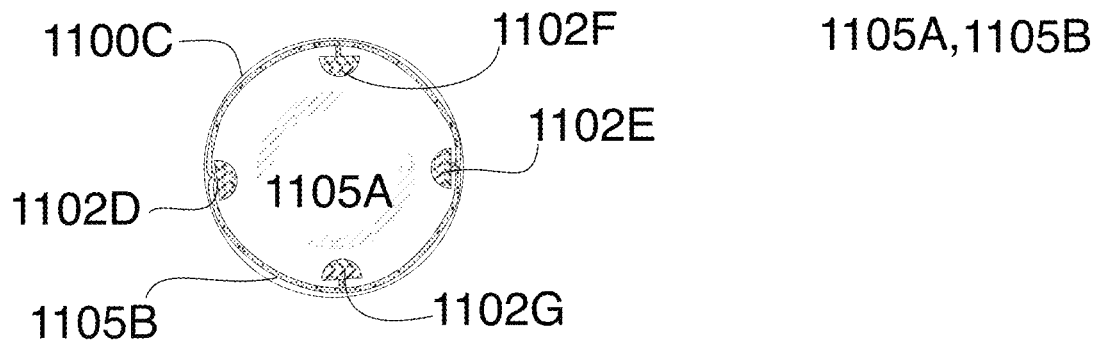

FIGS. 11B-11D illustrate one emitter 1102A, two emitters 1102B-1102C, and four emitters 1102D-1102G embedded in contact lenses 1100A-1100C, respectively.

In FIG. 11B, an active emitter 1102A is depicted coupled to two or more antenna lines 1105A-1105B around a segment of the circumference edge of the contract lens 1100A. The active emitter 1102A includes an integrated circuit 1106 with a processor/controller and other circuitry externally coupled to it or internally integrated on the integrated circuit. Alternatively, the emitter 1102A may be a passive emitter.

In FIG. 11C, a pair of passive emitters 1102B-1102C are depicted around a segment of the circumference edge of the contract lens 1100B. Alternatively, the emitters 1102B-1102C may be active emitters with two or more antenna feed 1105A-1105B in a segment near the circumference edge of the contract lens 1100B.

In FIG. 11D, a pair of active emitters 1102D-1102E and a pair of passive emitters 1102F-1102G are shown near the circumference edge of the contract lens 1100C. Alternatively, all emitters 1102D-1102G may be active emitters or passive emitters; just one may be passive with all others active; or just one may be active with all others passive.

Figure 11E:
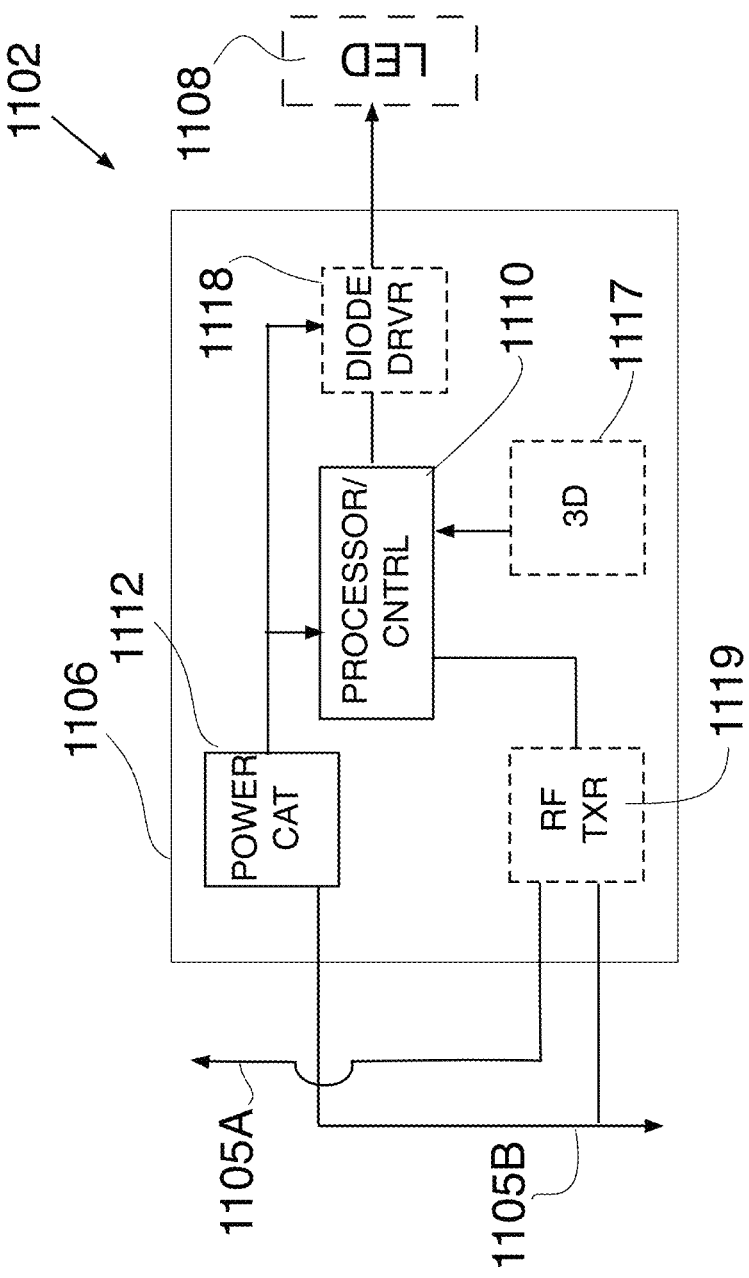
FIG. 11E is a functional block diagram of an active emitter device.

Referring now to FIG. 11E, further details of an instance of an active emitter 1102 are shown. The active emitter 1102A includes an integrated circuit 1106 with a processor/controller 1110 and other circuitry externally coupled to it or internally integrated on the integrated circuit coupled to the processor/controller 1110.

The integrated circuit (IC) 1106 can receive power over the antenna 1105A-1105B into a power conversion circuit 1112 coupled to the processor 1110. Radio frequency energy from an oscillating radio frequency (RF) signal is inductively coupled into the two or more antenna feeds 1105A-1105B by a nearby base antenna. The power conversion circuit 1112 can rectify and regulate the AC RF signals into a DC power source for other circuits within the IC 1106 as well as those coupled to it.

With a light emitting diode (LED) 1108 coupled to the integrated circuit 1106, a diode driver 1118 therein is coupled to and between the processor 1110 and the light emitting diode (LED) 1108. With power being generated by the power conversion circuit, the processor 1110 can generate a signal to activate the diode driver 1118. With power, the processor can activate the diode driver 11118 to drive and provide power to the light emitting diode 1108 to emit light out away from the eye of the user.

Alternatively or in addition to, the integrated circuit 1106 may have a 3D motion sensor 1117 coupled to the processor that directly senses eye motion. With power, the processor coupled to a radio transmitter/receiver (transceiver) 1109 can transmit and receive radio signals through the radio transceiver 1119 over the antenna lines 1105A-1105B. The base unit with its own corresponding radio transceiver can collect and further process the eye motion data.

Figure 11F:
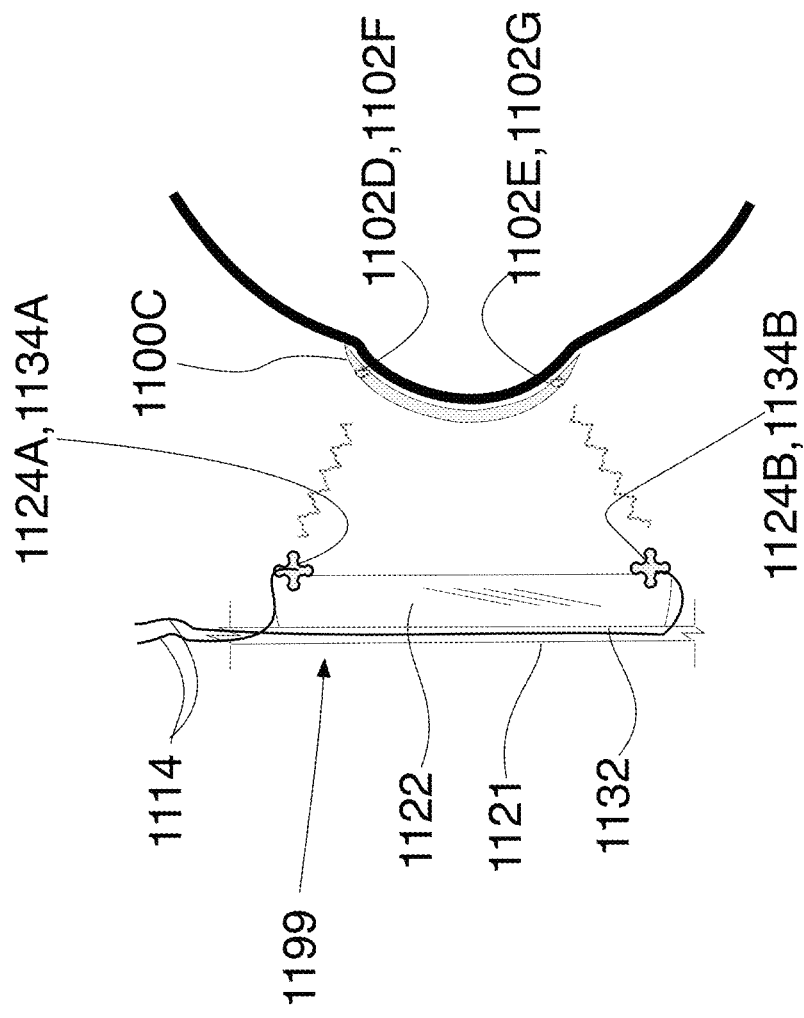
FIG. 11F is a side view of the sensing device near the contact lens mounted to the eyeball that may be used to capture data regarding eye movement of a user.

Referring now to FIG. 11F, for an active emitter, a base unit 1199 is shown including a frame 1121, a lens 1122, and poles of a base antenna 1124A-1124B wrapped around the lens 1122. Wires 1114 from the base antenna 1124A-1124B are coupled to a base radio receiver/transmitter (transceiver) (not shown), and then to a base processor (not shown) to process the captured eye motion signals.

With the base antenna 1124A-1124B of the base near the antenna lines 1105A-1105B of the contact lens, they can be inductively coupled together to transfer radio frequency power/energy as well as radio frequency signals between the base unit 1199 and the contact lens 1100C. When powered up, the eye motion captured by the motion sensor 1117 can be the communicated from the contact lens 1100C to the base unit 1199 by the radio transceivers in each.

For a passive emitter, the base unit 1199 (additionally or alternatively) includes one or more photo diode sensors 1134A-1134B coupled to the lens 1112 near its edges. The base unit 1199 may further include a light source 1132, such as a display device, to shine light towards one or more passive emitters 1102F,1102G. The light reflecting off the one or more passive emitters 1102F,1102G is captured by the one or more photo diode sensors 1134A-1134B to determine position and movement of an eye over time. Wires 1114 from the photo diode sensors 1134A-1134B are coupled to a base processor (not shown) to process the captured eye motion signals.

The base unit 1199 may be in the form of glasses (spectacles), VR goggles, a stand alone eye scanner, or a wall mounted eye scanner.

While an electronic device may be worn by a user adjacent a user's eye or eyes, such as in the case of glasses, goggles, and contact lenses; the electronic device to capture eye motions may be supported by a structure or a system with the user placing his/her eye or eyes near a video camera, sensors, or antenna to capture eye motions that include the involuntary eye micro-motions of interest.

Figure 12A:
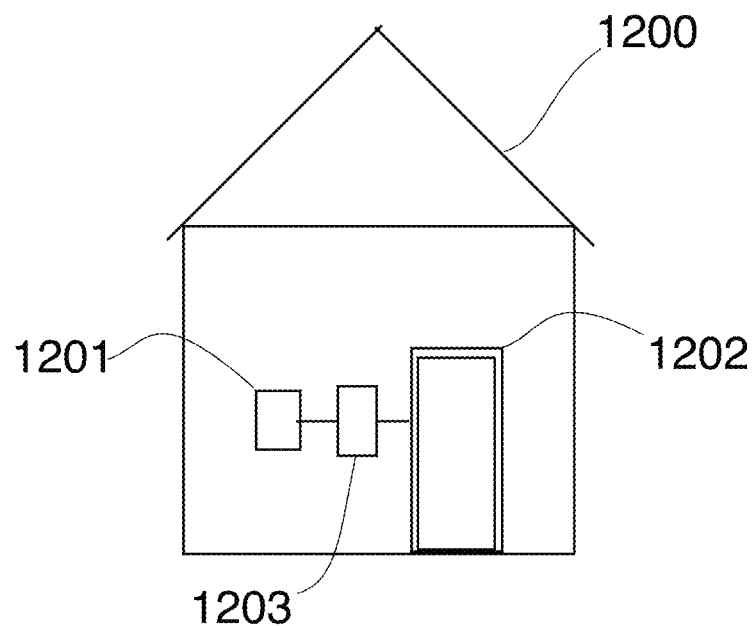
FIGS. 12A-12B illustrate an eye motion capture device affixed to a building structure to control access thereto.

FIG. 12A illustrate an eye motion capture device 1201 affixed to a building structure 1200 to control access to one or more doors 1202 in response to the involuntary eye micro-motions of a user. The eye motion capture device 1201 is coupled to an access system 1203 to control access to the one or more doors 1202 of the structure 1200. The access system 1203 can control unlocking one or more doors 1202 in response to proper involuntary eye micro-motions of the eye of an authorized user.

Figure 12B:
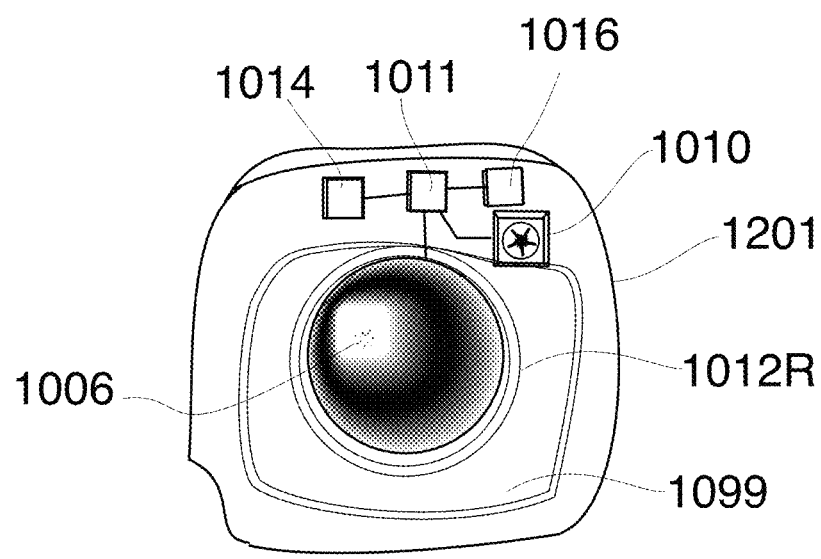

FIG. 12B illustrates a magnified view of the eye motion capture device 1201 that receives the area of the face of a user around the left or right eye. As discussed previously with reference to FIG. 10B, the eye motion capture device 1201 may include some similar structure and function of a processor 1011, as well as a video camera 1010, a display device 1012R and a memory 1014 coupled to the processor. The processor 1011 may be wired by a cable and a plug to the access system 1203. Alternatively, the processor 1011 may be wirelessly coupled to the access system 1203 by a radio 1016 coupled to the processor 1101.

Figure 13A:
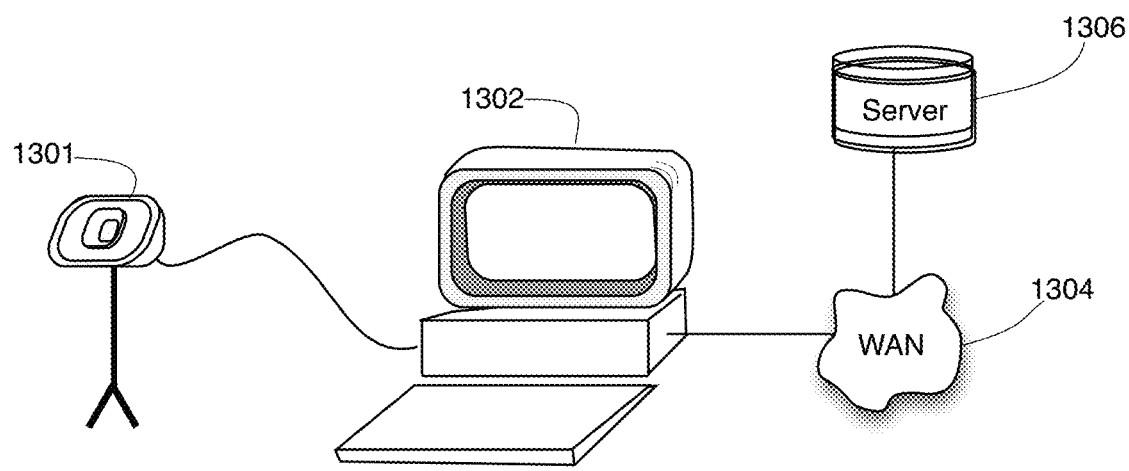
FIGS. 13A-13B illustrate a stand alone eye scanner to authenticate a user to a system.

FIG. 13A illustrates a stand alone eye scanner 1301 coupled to a system 1302 by wire with a cable or wirelessly with radios transmitter/receivers in each. The system 1302 may be coupled to a server 1306. The server may be remote and accessed over a wide area network 1304, such as the internet. The stand alone eye scanner 1301 can be used to non-invasively authenticate the user to the system 1302, and the server 1306, in response to the involuntary eye micro-motions of one or more eyes.

Figure 13B:
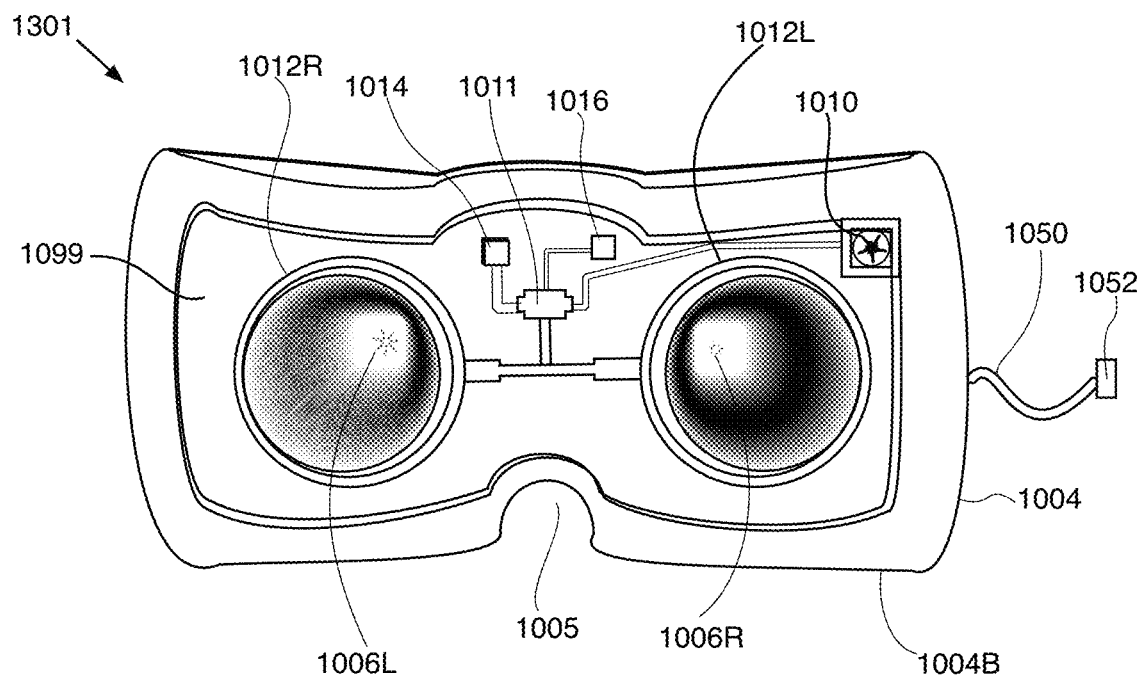

FIG. 13B illustrates a magnified view of the stand alone eye scanner 1301 that receives the eye area of the face of a user. As discussed previously with reference to FIG. 10B, the eye motion capture device 1301 similarly includes the structure and function of a processor 1011, as well as one or more video cameras 1010, a left display device 1012L, a right display device 1012R, and a memory 1014 coupled to the processor. The processor 1011 may be wired by a cable 1050 and a plug 1052 to the system 1302. Alternatively, a radio transmitter/receiver (transceiver) 1016 may be coupled to the processor 1011 so that the processor and headset/goggles can wirelessly be coupled to the system 1302. Left and/or right targets 1006L,1006R can be similarly generated on the left and/or right display devices 1012L,1012R so that the stand alone eye scanner 1301 can scan one or both eyes to non-invasively authenticate the user in response to the involuntary eye micro-motions of one or both eyes of the user.

In each of the electronic devices, the processor cooperates with another device to capture a representation of user eye movement from which the desired involuntary eye micro-motions can be extracted. The processor may further perform signal processing on the extracted involuntary eye micro-motions to determine identifying eye micro-motion features from the extracted involuntary eye micro-motions that are extracted and selected repeatedly by the same system, such as described in U.S. patent application Ser. No. 15/013,875; filed by Martin Zizi et al. on Feb. 2, 2016, incorporated herein by reference.

Identifying eye micro-motion features can be used with various systems that utilize user authentication. For example, the identifying eye micro-motion features can be classified in by a match percentage and used to authenticate a user with an authentication controller such as shown and described in U.S. patent application Ser. No. 15/013,875; filed by Martin Zizi et al. on Feb. 2, 2016, incorporated herein by reference. The identifying eye micro-motion features can be used to provide keyless access to homes, buildings, and vehicles such as shown and described in U.S. patent application Ser. No. 15/013,810; filed by Martin Zizi et al. on Feb. 2, 2016, incorporated herein by reference. The identifying eye micro-motion features can be used to encrypt/decrypt data such as shown and described in U.S. patent application Ser. No. 15/013,792; filed by Martin Zizi et al. on Feb. 2, 2016, incorporated herein by reference. The identifying eye micro-motion features can be used to secure access to privacy data, such as medical records shown and described in U.S. patent application Ser. No. 15/013,764; filed by Martin Zizi et al. on Feb. 2, 2016, incorporated herein by reference.

CONCLUSION

The embodiments of the invention are thus described. When implemented in software, the elements of the embodiments of the invention are essentially the code segments or instructions to perform the necessary tasks. The program or code segments/instructions can be stored in a processor readable medium for execution by a processor, such as processor 801. The processor readable medium may include any medium that can store information, such as memory 802. Examples of the processor readable medium include an electronic circuit, a semiconductor memory device, a read only memory (ROM), a flash memory, an erasable programmable read only memory (EPROM), a floppy diskette, a CD-ROM, an optical disk, or a hard disk. The program and code segments/instructions may be downloaded via computer networks such as the Internet, Intranet, etc.

While this specification includes many specifics, these should not be construed as limitations on the scope of the disclosure or of what may be claimed, but rather as descriptions of features specific to particular implementations of the disclosure. Certain features that are described in this specification in the context of separate implementations may also be implemented in combination in a single implementation. Conversely, various features that are described in the context of a single implementation may also be implemented in multiple implementations, separately or in sub-combination. Moreover, although features may be described above as acting in certain combinations and even initially claimed as such, one or more features from a claimed combination may in some cases be excised from the combination, and the claimed combination may be directed to a sub-combination or variations of a sub-combination. Accordingly, the claimed invention is limited only by patented claims that follow below.

What is claimed is:

1. A method of securing data, the method comprising:
capturing eye motion of an eye of a first authorized user to generate a first multi-dimensional eye motion signal;
extracting involuntary eye motion from the first multidimensional eye motion signal;
generating a first neurological eye print in response the involuntary eye motion and first user calibration parameters; and
encrypting data with an encryption algorithm using the first neurological eye print as an encryption key;
storing the first neurological eye print in a secured storage device associated with the first neurological eye print and one or more secondary neurological eye prints,
wherein the stored neurological eye print is accessible from the secured storage device in response to the first neurological eye print regenerated from the first authorized user, and
wherein the stored neurological eye print is further accessible from the secured storage device in response to the one or more secondary neurological eye prints generated from one or more secondary authorized users differing from the first authorized user;
accessing the encrypted data that is encrypted with the first neurological eye print as the encryption key including
capturing eye motion of an eye of a one or more secondary authorized users to generate a second multi-dimensional eye motion signal;
extracting involuntary eye motion from the second multidimensional eye motion signal;
in response to the second multi-dimensional eye motion signal,
regenerating a second neurological eye print of the one of the one or more secondary authorized users;
determining a live match percentage in response to the second regenerated neurological eye print and the second user calibration parameters associated with the one of the one or more secondary authorized users; and
in response to the live match percentage being greater than or equal to a live access match level, verifying the one of the one or more secondary authorized users to provide access of the stored neurological eye print in the secured storage device.

2. The method of claim 1, further comprising
accessing the encrypted data that is encrypted with the first neurological eye print as the encryption key including
capturing eye motion of an eye of the first authorized user to generate a second multi-dimensional eye motion signal;
extracting involuntary eye motion from the second multidimensional eye motion signal;
regenerating the first neurological eye print in response to the second the multi-dimensional eye motion signal;
determining a match percentage in response to the first regenerated neurological eye print and the first user calibration parameters; and
in response to the match percentage being greater than or equal to an access match level, decrypting data with the encryption algorithm using the first regenerated neurological eye print representing the first encryption key.

3. The method of claim 2, wherein
the encrypted data is stored on a remote server; and
the first user is remotely verified over a computer network to decrypt the encrypted data.

4. The method of claim 1, wherein
the first authorized user invites the one or more secondary authorized users to have access to the stored neurological eye print in response to verification of the one or more secondary authorized users with their respective one or more secondary neurological eye prints.

5. The method of claim 1, wherein the accessing of the encrypted data that is encrypted with the first neurological eye print as the encryption key further includes
in response to verification of the one of the one or more secondary authorized users, accessing the stored neurological eye print from the secured storage device;
determining a stored match percentage in response to the stored neurological eye print and the first user calibration parameters; and
in response to the stored match percentage being greater than or equal to a stored access match level, decrypting data with the encryption algorithm using the stored neurological eye print representing the encryption key.

6. The method of claim 5, wherein
the stored access match level is less than or equal to the live access match level.

7. The method of claim 5, wherein
the encrypted data is stored on a remote server; and
the one of the one or more secondary authorized users is remotely verified over a computer network to access the stored neurological eye print in the secured storage device and decrypt the encrypted data.

8. The method of claim 1, wherein
the multi-dimensional motion of the body part is at least two dimensional motion and the multi-dimensional signal is at least a two dimensional signal.

9. The method of claim 1, wherein
the secured storage device is a portable secured storage device.

* * * * *